United States Patent
Mullin

(10) Patent No.: US 10,821,073 B1
(45) Date of Patent: *Nov. 3, 2020

(54) EDIBLE ANIMAL MEDICINE CONTAINER

(71) Applicant: Make Ideas, LLC, La Jolla, CA (US)

(72) Inventor: Keith Alan Mullin, La Jolla, CA (US)

(73) Assignee: Make Ideas, LLC, La Jolla, CA (US)

( * ) Notice: Subject to any disclaimer, the term of this patent is extended or adjusted under 35 U.S.C. 154(b) by 97 days.

This patent is subject to a terminal disclaimer.

(21) Appl. No.: 15/940,569

(22) Filed: Mar. 29, 2018

Related U.S. Application Data

(63) Continuation-in-part of application No. 15/201,127, filed on Jul. 1, 2016, now Pat. No. 9,931,297, which is a continuation of application No. 14/502,636, filed on Sep. 30, 2014, now Pat. No. 9,498,433.

(60) Provisional application No. 62/478,330, filed on Mar. 29, 2017, provisional application No. 62/485,352, filed on Apr. 13, 2017, provisional application No. 61/884,343, filed on Sep. 30, 2013.

(51) Int. Cl.
*A61K 9/00* (2006.01)
*A61K 9/20* (2006.01)
*A61D 7/00* (2006.01)

(52) U.S. Cl.
CPC .............. *A61K 9/0056* (2013.01); *A61D 7/00* (2013.01); *A61K 9/00* (2013.01); *A61K 9/2072* (2013.01)

(58) Field of Classification Search
None
See application file for complete search history.

(56) References Cited

U.S. PATENT DOCUMENTS

| | | | |
|---|---|---|---|
| 4,831,058 A | 5/1989 | Pankhania et al. | |
| 5,792,470 A | 8/1998 | Baumgardner, Sr. | |
| 5,853,757 A | 12/1998 | Durand et al. | |
| 5,895,662 A | 4/1999 | Meyer | |
| 5,928,213 A | 7/1999 | Barney et al. | |
| 6,143,316 A | 11/2000 | Hayden et al. | |
| 6,211,246 B1 | 4/2001 | Gelotte et al. | |
| 6,423,357 B1 * | 7/2002 | Woods | A47G 19/2205 426/104 |
| 8,501,218 B2 | 8/2013 | Hurwitz | |
| 8,904,966 B2 | 12/2014 | Kolozsvari et al. | |
| 9,498,433 B1 | 11/2016 | Mullin et al. | |
| 9,931,297 B1 * | 4/2018 | Mullin | A61K 9/0056 |
| 2002/0139708 A1 | 10/2002 | Lien | |
| 2005/0092641 A1 | 5/2005 | Marsden et al. | |
| 2005/0169972 A1 * | 8/2005 | Hasirci | A61J 7/0061 424/442 |
| 2008/0302802 A1 | 12/2008 | Ramsden | |
| 2011/0256208 A1 | 10/2011 | Ling | |
| 2012/0321706 A1 | 12/2012 | Masri et al. | |

OTHER PUBLICATIONS

Merriam-Webster Dictionary, volume definition, obtained online at: http://www.merriam-webster.com/dictionary/volume, downloaded on Mar. 30, 2016, pp. 1-4.

* cited by examiner

*Primary Examiner* — Abigail Vanhorn
(74) *Attorney, Agent, or Firm* — Tillman Wright, PLLC; James D. Wright; David R. Higgins

(57) ABSTRACT

An edible animal medicine container for delivering medicine or other ingestible material, contained therein, to an animal, includes first and second edible housing shells. The first shell include a first opening defined by a first peripheral ledge having a periphery that is surrounded by a second peripheral ledge that is stepped down from, and connected via a first wall to, the first peripheral ledge. A peripheral lip is disposed around the first wall. The second shell includes a second opening defined by a third peripheral ledge surrounding, and connected via a second wall to, a fourth peripheral ledge which is recessed into the second opening. The first and second shells are positionable into a closed state wherein the first peripheral ledge, the first wall, and the peripheral lip are inserted into the second opening so as to retain the ingestible material within the interior until ingested by an animal.

17 Claims, 39 Drawing Sheets

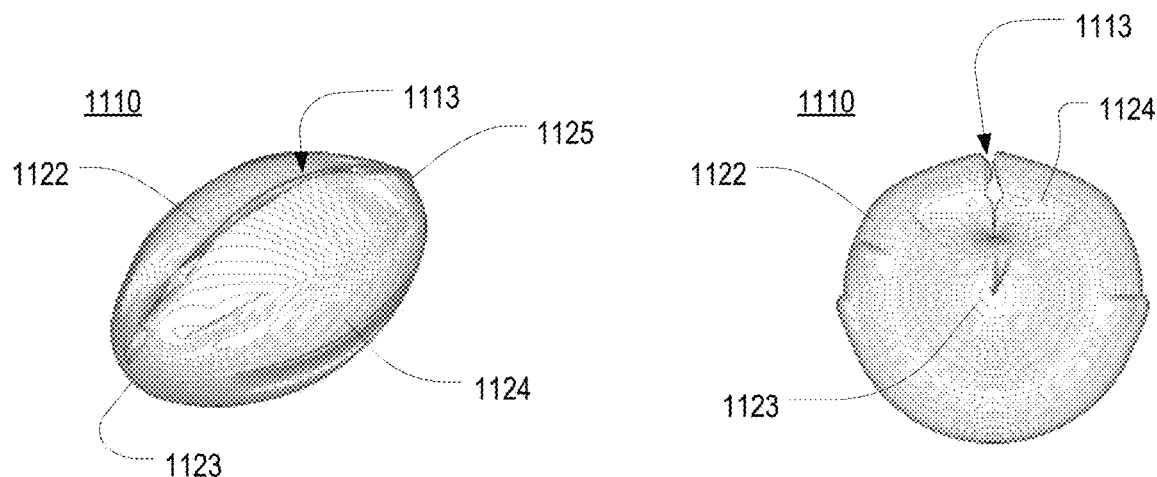
FIG. 92   FIG. 93
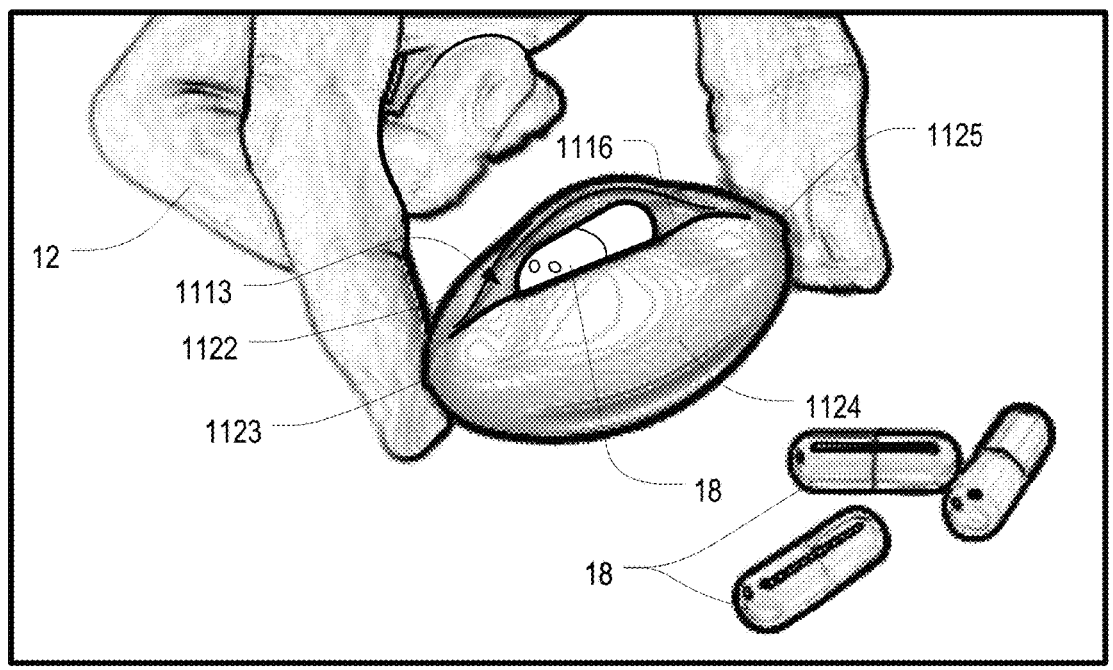
FIG. 94

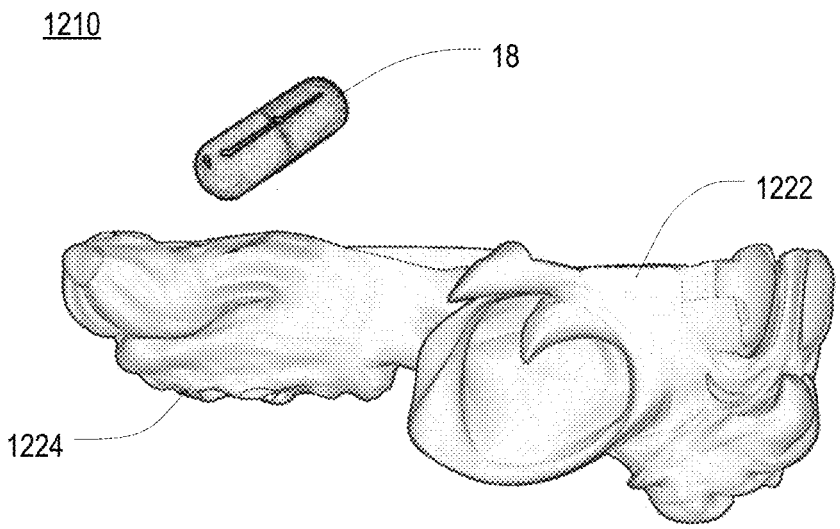
FIG. 95
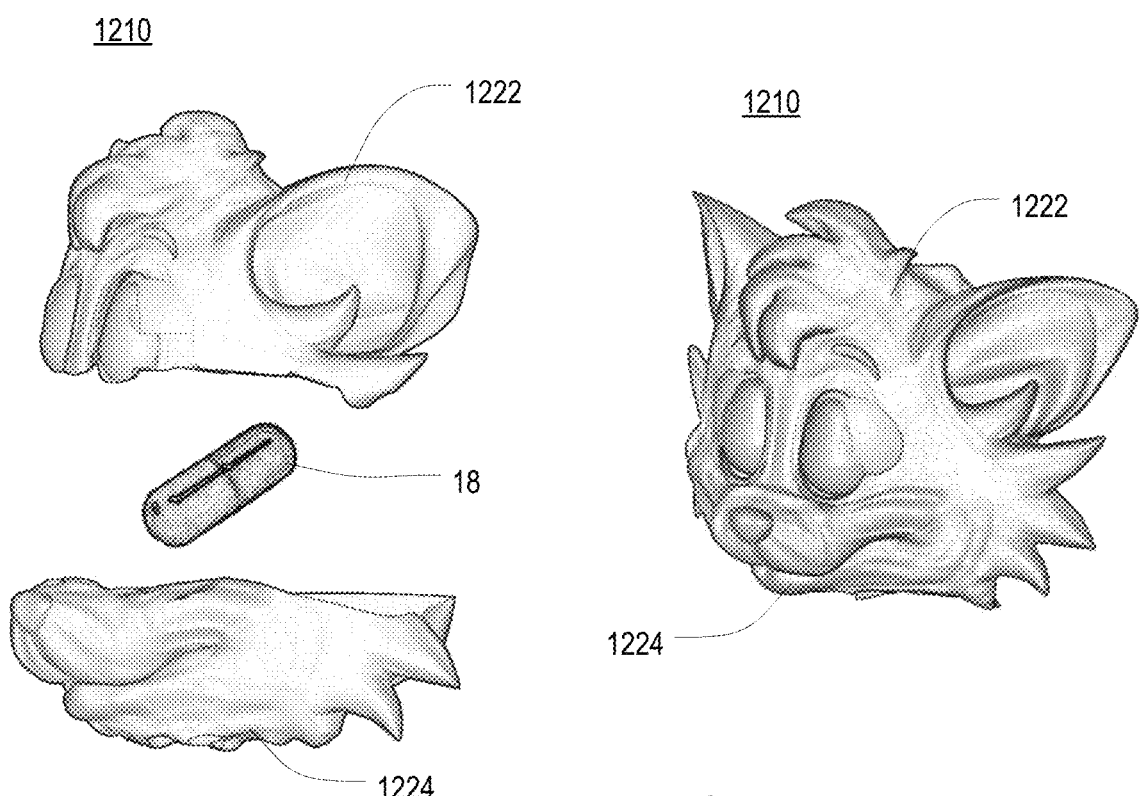
FIG. 96
FIG. 97

EDIBLE ANIMAL MEDICINE CONTAINER

CROSS-REFERENCE TO RELATED APPLICATION

The present application is:

(a) a U.S. nonprovisional patent application of, and claims priority under 35 U.S.C. § 119(e) to, U.S. provisional patent application Ser. No. 62/478,330, filed Mar. 29, 2017, and U.S. provisional patent application Ser. No. 62/485,352, filed Apr. 13, 2017, which provisional patent applications are incorporated by reference herein; and (b) a U.S. continuation-in-part patent application of, and claims priority under 35 U.S.C. § 120 to, U.S. patent application Ser. No. 15/201,127, filed Jul. 1, 2016 (the "'127 application"), which '127 application issued Apr. 3, 2018 as U.S. Pat. No. 9,931,297, and which '127 application is a continuation of, and claims priority under 35 U.S.C. § 120 to, U.S. patent application Ser. No. 14/502,636, filed Sep. 30, 2014 (the "'636 application"), which '636 application issued Nov. 22, 2016 as U.S. Pat. No. 9,498,433, and which '636 application is a nonprovisional patent application of, and claims priority under 35 U.S.C. § 119(e) to, U.S. provisional patent application Ser. No. 61/884,343, filed Sep. 30, 2013.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE PRESENT INVENTION

Field of the Present Invention

The present invention relates generally to edible animal medicine containers, and in particular, to edible animal medicine containers that seal or partially seal a designated quantity of medicine or other ingestible material inside.

Background

A problem encountered by nearly pet owner and many other animal caretakers is the administration of oral medications and other ingestible materials to an animal. Animals frequently object to the taste, smell, texture, or the like of the material, or are generally distrustful of the person administrating the material or the manner in which it is administered.

A variety of techniques have been utilized to accomplish such administration. Simple techniques include disguising the pill or other material within a food that the animal is known to eat readily. For example, many dog and/or cat owners have hidden pills within a serving of peanut butter or rolled or buried within a slice of cheese or meat.

For administration of liquid medicines to animals, there are various syringes, spoons, sprayers and the like that are inserted into the animal's mouth and used to squirt or dispense such liquids into the animal's mouth. Unfortunately, animals tend to dislike these approaches for many reasons, including the feeling of being force fed, the taste of the medicine being dispensed, and the smell of the medicine.

More recently, edible food containers or carriers have been developed for such a purpose. Examples of such containers or carriers are describe, for example, in U.S. Pat. No. 5,792,470 (issued Aug. 11, 1998 to Baumgardner, Sr. and titled "EDIBLE CONTAINER FOR ADMINISTERING MEDICATION TO ANIMALS"), U.S. Pat. No. 6,143,316 (issued Nov. 7, 2000 to Hayden et al and titled "DIGESTIBLE POUCH AND METHOD FOR ADMINISTERING MEDICATIONS TO AN ANIMAL"), U.S. Pat. No. 8,501,218 (issued Aug. 6, 2013 to Hurwitz and titled "EDIBLE CHEW PILL JACKET"), and U.S. Patent Publication No. US2011/0256208 A1 (issued Oct. 20, 2011 to Ling and titled "EDIBLE CARRIER FOR ANIMAL MEDICATION"), each of which is incorporated its entirety by reference and a copy of each of which is attached hereto as an appendix. However, these devices suffer from various shortcomings, including inability to disguise or contain the smell of the pills or medicine contained therein, inability to assist in measuring a volume or quantity of medicine or other material, not being watertight or water sealed, and the like. Smell, in particular, has recently gained notice as a significant factor in whether an animal such as a dog or cat is willing to ingest a particular medicine, pill or other substance, as a dog's sense of smell is upwards of 40 times as acute as a human's, and non-watertight or water sealed containers fail to potentially prevent a dog from being able to pick up the scent of medicines or other ingestible materials disposed inside.

Thus, a need exists for further improvement in edible animal medicine containers, such as but not limited to means for easier measuring and loading.

SUMMARY OF THE PRESENT INVENTION

Some exemplary embodiments of the present invention may overcome one or more of the above disadvantages and other disadvantages not described above, but the present invention is not required to overcome any particular disadvantage described above, and some exemplary embodiments of the present invention may not overcome any of the disadvantages described above.

Broadly defined, the present invention according to one aspect is an edible animal medicine container for delivering medicine or other ingestible material, contained therein, to an animal, including: a first edible housing shell that includes a first peripheral ledge, surrounding a first central hollow, and a first interlocking feature extending therefrom; and a second edible housing shell that includes a second peripheral ledge, surrounding a second central hollow, and a second interlocking feature extending into, and at least partially defined by, the second peripheral ledge; wherein the second edible housing shell is positionable relative to, and connectable to, the first edible housing shell to define an interior in which medicine or other ingestible material may be disposed by a user; and wherein in such connected state the first interlocking feature is seated and frictionally held within the second interlocking feature of the second edible housing shell so as to retain the first and second edible housing shells together and thereby retain the medicine or other ingestible material within the interior until ingested by an animal.

In a feature of this aspect, the first interlocking feature is a standing wall or ledge extending in a generally perpendicular direction from the first peripheral ledge, wherein the second interlocking feature is a recessed ledge extending into, and at least partially defined by, the second peripheral ledge, and wherein, in the connected state, the standing wall or ledge of the first edible housing shell is seated and frictionally held within the recessed ledge of the second edible housing shell so as to retain the first and second edible housing shells together and thereby retain the medicine or other ingestible material within the interior until ingested by an animal.

In a further feature, in the connected state, the first peripheral ledge is in direct contact with the second peripheral ledge, thereby closing a gap between the first and second edible housing shells and preventing liquids placed in the container from flowing and leaking out of the container. In further features, the recessed ledge is adjacent the second central hollow; in an unconnected state the recessed ledge opens directly into the second central hollow; the recessed ledge is completely surrounded and defined by the second peripheral ledge; and/or the first peripheral ledge is flared outward relative to the rest of an exterior of the first edible housing shell, and wherein the second peripheral ledge is flared outward relative to the rest of an exterior of the second edible housing shell.

In another further feature, at least one of the first and second edible housing shells has an interior volume of a known predetermined standard size so as to facilitate measurement of a volume of ingestible material to be disposed in the interior of the container. In further features, the interior volume of at least one of the first and second edible housing shells is one U.S. tablespoon; the interior volume of at least one of the first and second edible housing shells is one U.S. teaspoon; the first edible housing shell has an interior volume of a first standard amount, and the second edible housing shell has an interior volume of a second standard amount; the interior volume of the first edible housing shell is one U.S. teaspoon; and/or at least one of the first and second edible housing shells is marked with predetermined units of measurement.

In another further feature, in at least an initial open state, the two shells are integrally connected together. In further features, an edge of the first shell is initially connected directly to an edge of the second shell; the two shells are connected together at least initially via an edible hinge or tether; and/or the edible hinge or tether is adapted to hold the two shells together until the edible hinge or tether is intentionally snapped by a user so as to close the two shells.

In another further feature, the two shells are approximately the same size. In a further feature, the two shells are identical to each other.

In another further feature, the standing wall or ledge is a first standing wall or ledge; the recessed ledge is a first recessed ledge; the first shell further includes a second recessed ledge extending into, and at least partially defined by, the first peripheral ledge; the second shell further includes a second standing wall or ledge extending in a general perpendicular direction from the second peripheral ledge; and in the connected state, the standing wall of the second edible housing shell is seated and frictionally held within the recessed ledge of the first edible housing shell so as to retain the first and second edible housing shells together and thereby retain the medicine or other ingestible material within the interior until ingested by an animal. In a further feature, the first and second shells each include opposed first and second lateral sides; the first standing wall or ledge is located along the first lateral side of the first shell; the second recessed ledge is located along the second lateral side of the first shell; the second standing wall or ledge is located along the first lateral side of the second shell; and the first recessed ledge is located along the second lateral side of the second shell.

In another further feature, the standing wall or ledge includes a plurality of cylindrical pegs, wherein the recessed ledge includes a corresponding plurality of cylindrical recesses, and wherein, in the connected state, the cylindrical pegs of the first edible housing shell are seated and frictionally held within the cylindrical recesses of the second edible housing shell so as to retain the first and second edible housing shells together and thereby retain the medicine or other ingestible material within the interior until ingested by an animal.

In another further feature, the first edible housing shell is connected to the second edible housing shell with a threaded helical structure and the two shells are screwed together. In a further feature, the first housing shell includes a screw thread in the form of a ridge wrapped around a cylinder or cone in the form of a helix.

In another feature of this aspect, the first and second edible housing shells are sufficiently interlocked to provide a temporary water seal sufficient to prevent liquid medicine or other ingestible material disposed by a user therein from leaking therefrom until the container is ingested by the animal. In further features, the first and second edible housing shells are sufficiently interlocked to withstand internal hydrostatic pressure up to 1 PSI; and/or the first and second edible housing shells are sufficiently interlocked to withstand internal hydrostatic pressure up to 5 PSI.

Broadly defined, the present invention according to another aspect is an edible animal medicine container for delivering medicine or other ingestible material, contained therein, to an animal, including: a first edible housing shell; a second edible housing shell that is positionable relative to, and connectable to, the first edible housing shell to define an interior in which medicine or other ingestible material may be disposed by a user; wherein at least one of the first and second edible housing shells has an interior volume of a known predetermined standard size so as to facilitate measurement of a volume of ingestible material to be disposed in the interior of the container.

In a feature of this aspect, the interior volume of at least one of the first and second edible housing shells is one U.S. tablespoon.

In another feature of this aspect, the interior volume of at least one of the first and second edible housing shells is one U.S. teaspoon.

In another feature of this aspect, the interior volume of the first edible housing shell is one U.S. teaspoon, and the interior volume of the second edible housing shell is one U.S. tablespoon.

In another feature of this aspect, at least one of the first and second edible housing shells is marked with predetermined units of measurement.

In another feature of this aspect, the container further includes an edible hinge or tether connecting the two shells together. In a further feature, the edible hinge or tether is adapted to hold the two shells together until the edible hinge or tether is intentionally snapped by a user so as to close the two shells.

In another feature of this aspect, the two shells are adapted to be coupled together until the container is delivered to a digestive tract of an animal. In further features, a rim on one of the two edible housing shells is adapted to be friction fit or snap fit within a rim on the other of the two edible housing shells; a first latch structure is disposed on one of the two edible housing shells and a second latch structure, adapted to mate with the first latch structure, is disposed on the other of the two edible housing shells; a male threaded fitting is disposed on one of the two edible housing shells and female threaded fitting, adapted to be screw-coupled to the male threaded fitting, is disposed on the other of the two edible housing shells; and/or the two shells are coupled together such that a liquid placed in the container is prevented from flowing and leaking out of the container.

In another feature of this aspect, the housing is egg-shaped.

In another feature of this aspect, the housing is bone-shaped.

Broadly defined, the present invention according to another aspect is an edible animal medicine container for delivering medicine or other ingestible material, contained therein, to an animal, including: an edible housing, including two shells, at least one of the shells having a central hollow; and an edible hinge or tether connecting the two shells together; wherein the two shells may be coupled together in a closed state to define an interior in which medicine or other ingestible material may be disposed by a user.

In a feature of this aspect, the two shells of the edible housing are initially provided in an uncoupled, open state.

In another feature of this aspect, the edible hinge or tether is a living hinge.

In another feature of this aspect, at least one of the two edible housing shells has an interior volume of a known predetermined standard size so as to facilitate measurement of a volume of ingestible material to be disposed in the interior of the container. In further features, the interior volume of at least one of the two edible housing shells is one U.S. tablespoon; the interior volume of at least one of the two edible housing shells is one U.S. teaspoon; and/or the interior volume of a first edible housing shell is one U.S. teaspoon, and the interior volume of a second edible housing shell is one U.S. tablespoon.

In another feature of this aspect, at least one of the first and second edible housing shells is marked with predetermined units of measurement.

In another feature of this aspect, the two shells are adapted to be coupled together until the container is delivered to a digestive tract of an animal. In further features, a rim on one of the two edible housing shells is adapted to be friction fit or snap fit within a rim on the other of the two edible housing shells; a first latch structure is disposed on one of the two edible housing shells and a second latch structure, adapted to mate with the first latch structure, is disposed on the other of the two edible housing shells; a male threaded fitting is disposed on one of the two edible housing shells and female threaded fitting, adapted to be screw-coupled to the male threaded fitting, is disposed on the other of the two edible housing shells; and/or the two shells are coupled together such that a liquid placed in the container is prevented from flowing and leaking out of the container In another feature of this aspect, the housing is egg-shaped.

In another feature of this aspect, the housing is bone-shaped.

In another feature of this aspect, the edible hinge or tether is adapted to hold the two shells together until the edible hinge or tether is intentionally snapped by a user so as to close the two shells.

Broadly defined, the present invention according to another aspect is a method of administering a medicine or other ingestible material to an animal, including: providing an edible animal medicine container having an edible housing, including two shells connected by a hinge or tether, defining an interior; opening the two hinged or tethered shells; loading medicine or other ingestible material into the interior of the housing; closing the two shells together such that the medicine or other ingestible material is retained inside; and delivering the closed container to an animal such that the medicine or other ingestible material remains within the housing as the container enters the digestive tract of the animal.

In a feature of this aspect, the two shells remain hinged or tethered during the opening and loading steps. In further features, the two shells remain hinged or tethered during the opening, loading, and closing steps; and/or the method further includes a step, before closing the two shells together, of breaking the hinge or tether to enable the two shells to be closed together.

In another feature of this aspect, at least one of the provided edible housing shells has an interior volume of a known predetermined standard size so as to facilitate measurement of a volume of ingestible material to be disposed in the interior of the container. In further features, the interior volume of at least one of the provided edible housing shells is one U.S. tablespoon; the interior volume of at least one of the two edible housing shells is one U.S. teaspoon; and/or the interior volume of a first edible housing shell is one U.S. teaspoon, and the interior volume of a second edible housing shell is one U.S. tablespoon.

In another feature of this aspect, at least one of the provided edible housing shells is marked with predetermined units of measurement.

In another feature of this aspect, the step of loading the medicine or other ingestible material into the interior of the housing includes measuring a desired amount of the medicine or other ingestible material by filling at least one housing shell to a predetermined level that is indicated by the housing shell.

In another feature of this aspect, the step of loading medicine or other ingestible material into the interior of the housing includes loading a liquid medicine or other ingestible material into the interior of the housing, and the step of closing includes preventing the flow and leakage of the liquid out of the housing.

Broadly defined, the present invention according to another aspect is an edible animal medicine container for delivering medicine or other ingestible material, contained therein, to an animal, including: a first edible housing shell that includes a first opening defined by a first peripheral ledge wherein the first peripheral ledge has a periphery, wherein the periphery of the first peripheral ledge is surrounded by a second peripheral ledge that is stepped down from the first peripheral ledge, wherein the periphery of the first peripheral ledge is connected to the second peripheral ledge via a first wall, and wherein a peripheral lip is disposed around the first wall and extends outward therefrom; a second edible housing shell that includes a second opening defined by a third peripheral ledge, wherein the third peripheral ledge surrounds a fourth peripheral ledge that is recessed into the second opening, and wherein the periphery of the fourth peripheral ledge is connected to the third peripheral ledge by a second wall; wherein the second edible housing shell is positionable relative to the first edible housing shell in a closed state to define an interior in which medicine or other ingestible material may be disposed by a user; wherein in such closed state the first peripheral ledge, the first wall, and the peripheral lip are inserted into the second opening such that: (i) the first peripheral ledge is placed within close proximity of the fourth peripheral ledge inside the second opening, (ii) the third peripheral ledge is placed within close proximity of the second peripheral ledge, and (iii) the second wall is placed in contact with the first wall, including the peripheral lip; and wherein in such closed state the second edible housing shell is seated and held on the first edible housing shell so as to retain the first and second edible housing shells together and thereby retain the medicine or other ingestible material within the interior until ingested by an animal.

In a feature of this aspect, a peripheral groove extends into the second wall such that the closed state peripheral lip around the first wall fits into, and is retained in, the peripheral groove of the second wall so as to retain the first and second edible housing shells together.

In another feature of this aspect, in the closed state, the first peripheral ledge is in direct contact with the fourth peripheral ledge, thereby closing a gap between the first and second edible housing shells and preventing liquids placed in the container from flowing and leaking out of the container.

In another feature of this aspect, the two shells are integrally connected together in at least an initial open state. In further features, an edge of the first edible housing shell is initially connected directly to an edge of the second edible housing shell; the first and second edible housing shells are connected together at least initially via an edible hinge or tether; and/or the edible hinge or tether is adapted to hold the two shells together until the edible hinge or tether is snapped by a user so as to close the two shells.

In another feature of this aspect, the first edible housing shell defines a central hollow, wherein the first opening is in fluid communication with, and provides access to, the central hollow, and wherein the central hollow forms the predominant portion of the interior of the container in the closed state. In further features, the second edible housing shell serves as a cap to cover the first opening and the central hollow of the first edible housing shell; the central hollow is defined by interior surfaces of first edible housing shell, and wherein the interior surfaces include a plurality of surface features, extending or rising from surrounding portions of the interior surfaces to receive and retain pill or capsule-form medicine in the central hollow; the surface features are ribs extending longitudinally along the central hollow interior surfaces; and/or the surface features are one-way barbs extending from the central hollow interior surfaces.

Broadly defined, the present invention according to another aspect is an edible animal medicine container for delivering medicine or other ingestible material, contained therein, to an animal, including: a first edible housing shell that includes a first opening defined by a first peripheral ledge wherein the first peripheral ledge has a periphery, wherein the periphery of the first peripheral ledge is surrounded by a second peripheral ledge that is stepped down from the first peripheral ledge, and wherein the periphery of the first peripheral ledge is connected to the second peripheral ledge via a first wall; a second edible housing shell that includes a second opening defined by a third peripheral ledge, wherein the third peripheral ledge surrounds a fourth peripheral ledge that is recessed into the second opening, and wherein the periphery of the fourth peripheral ledge is connected to the third peripheral ledge by a second wall; wherein at least one of the first and second edible housing shells defines a central hollow, wherein the first or second opening, respectively, is in fluid communication with, and provides access to, the central hollow, wherein the central hollow is defined by interior surfaces of first or second edible housing shell, respectively, and wherein the interior surfaces include a plurality of surface features, extending or rising from surrounding portions of the interior surfaces to receive and retain pill or capsule-form medicine in the central hollow; wherein the second edible housing shell is positionable relative to the first edible housing shell in a closed state to define an interior, including the central hollow, in which medicine or other ingestible material may be disposed by a user; wherein in such closed state the first peripheral ledge and the first wall are inserted into the second opening such that: (i) the first peripheral ledge is placed within close proximity of the fourth peripheral ledge inside the second opening, (ii) the third peripheral ledge is placed within close proximity of the second peripheral ledge, and (iii) the second wall is placed in contact with the first wall; and wherein in such closed state the second edible housing shell is seated and held on the first edible housing shell so as to retain the first and second edible housing shells together and thereby retain the medicine or other ingestible material within the interior, including the central hollow, until ingested by an animal.

In another feature of this aspect, the surface features are ribs extending longitudinally along the central hollow interior surfaces. In a further feature, the ribs receive and retain pill or capsule-form medicine in the central hollow such that an air gap exists between surfaces of the medicine and the surrounding portions of the central hollow interior surfaces.

In another feature of this aspect, the surface features are one-way barbs extending from the central hollow interior surfaces. In a further feature, the one way barbs are arranged in tiers and wherein each one-way barb includes a tooth-like structure at the end of a flexible arm.

In another feature of this aspect, in the closed state, the first peripheral ledge is in direct contact with the fourth peripheral ledge, thereby closing a gap between the first and second edible housing shells and preventing liquids placed in the container from flowing and leaking out of the container.

In another feature of this aspect, the two shells are integrally connected together in at least an initial open state.

In another feature of this aspect, a peripheral lip is disposed around the first wall and extends outward therefrom, wherein a peripheral groove extends into the second wall such that the closed state peripheral lip around the first wall fits into, and is retained in, the peripheral groove of the second wall so as to retain the first and second edible housing shells together.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein:

FIG. 92 is a perspective view of another alternative edible pet medicine container, shown in a closed state, in accordance with one or more preferred embodiments of the present invention;

FIG. 93 is an end view of the edible pet medicine container of FIG. 92;

FIG. 94 is a perspective view of a user squeezing the edible pet medicine container of FIG. 92 into an open state;

FIG. 95 is a side view of another alternative edible pet medicine container, shown in an initial state, provided in the shape of a whimsical character in accordance with one or more preferred embodiments of the present invention;

FIG. 96 is a side view of the edible pet medicine container of FIG. 95, shown in a separated state; and FIG. 97 is a perspective view of the edible pet medicine container of FIG. 95, shown in a closed state.

DETAILED DESCRIPTION

Figure 1:
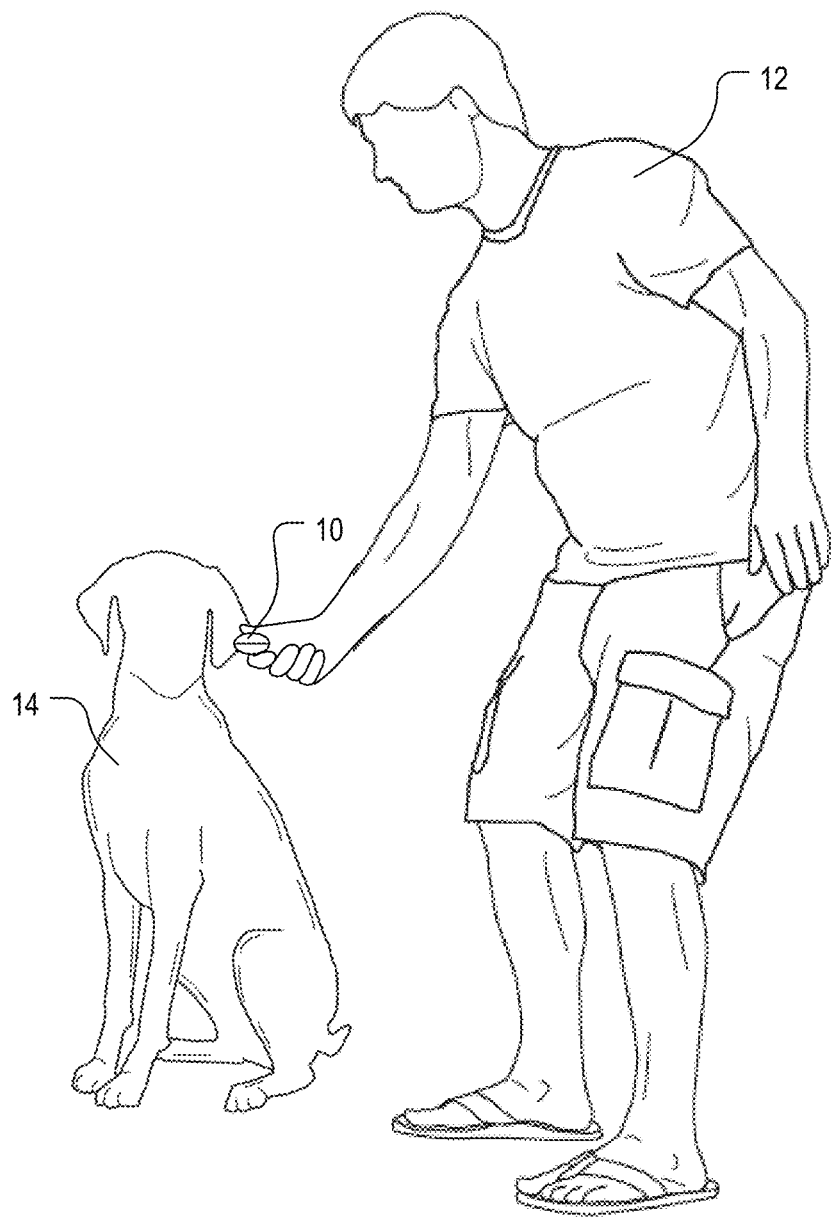
FIG. 1 is a perspective view of a man feeding medicine contained in an edible animal medicine container to a pet, such as a canine, in accordance with one or more preferred embodiments of the present invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers," "a picnic basket having crackers without cheese," and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, one or more preferred embodiments of the present invention are next described. The following description of one or more preferred embodiment(s) is merely exemplary in nature and is in no way intended to limit the invention, its application, or uses.

FIG. 1 is a perspective view of a man 12 feeding medicine or other ingestible material contained in an edible animal medicine container 10 to a pet 14 in accordance with one or more preferred embodiments of the present invention. The container 10 serves as a delivery device or mechanism for an ingestible material contained inside. The ingestible material may be a medicine, drug, pharmaceutical, vitamin, supplement, herb, x-ray dye, butter, paste, gel, powder, or the like. The medicine may be in the form of a hard (e.g. pill) or soft (e.g. paste, gel, or the like) solid, a liquid, a powder material, a granular material, or the like, and the container 10 may be flavored, scented, colored, and/or otherwise designed to appeal to a pet. As described below, the container 10 thus provides an effective way to ensure and encourage the ingestion of the medicine, in whatever form, by a pet or other animal.

Figure 2:
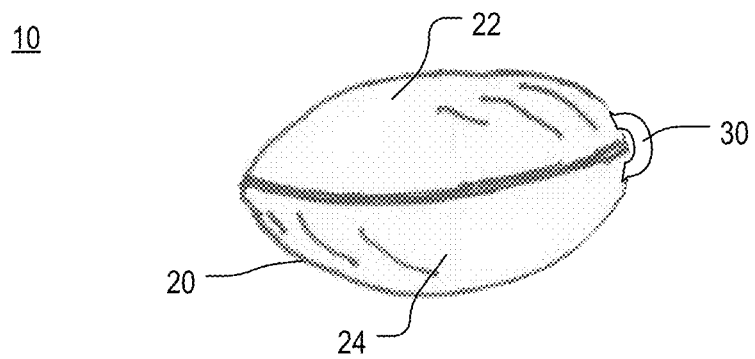
FIG. 2 is a perspective view of an edible pet medicine container of the type shown in FIG. 1, shown in a closed configuration.
Figure 3:
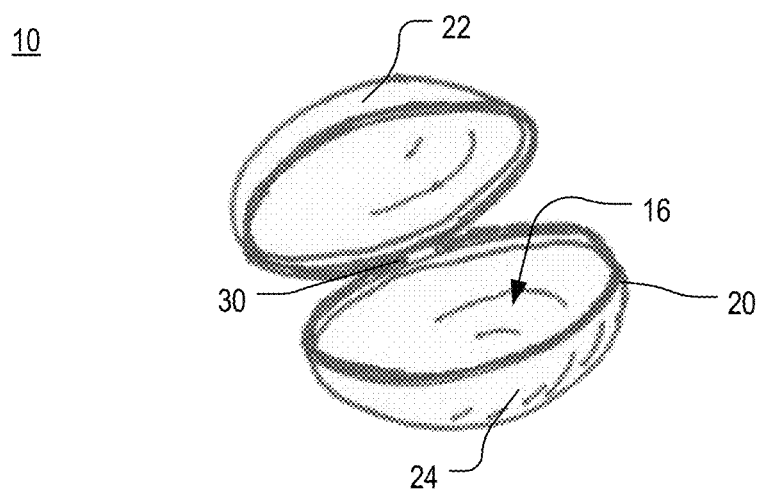
FIG. 3 is a perspective view of the edible pet medicine container of FIG. 2, shown in a partially open configuration.

FIG. 2 is a perspective view of an edible pet medicine container 10 of the type shown in FIG. 1, shown in a closed configuration, and FIG. 3 is a perspective view of the edible pet medicine container 10 of FIG. 2, shown in a partially open configuration. As shown therein, the container 10 includes a housing 20, defining an interior 16, and a hinge or tether 30. The housing 20 includes an upper shell 22 and a lower shell 24, which at least for convenience may be referred to herein as an upper half and a lower half. The housing halves are shaped such that when closed, the housing is somewhat egg-shaped. The rounded exterior of such housing shape advantageously avoids corners and edges that might be unappealing to the animal ingesting the container 10, but it will be appreciated that other shapes, including simple shapes, such as spherical, oblong, pill-shaped, or the like, and complex shapes, such as "bone"-shaped, animal-shaped (full scale or miniature, and including a cat shape, a bird shape, a rabbit shape, a squirrel shape, and/or a bear shape) may alternatively be utilized. The exterior surface of the housing 20 may be smooth or rough, and/or may have contours and texturing that mimics various other materials. For example, in various embodiments, the exterior surface of the housing 20 may mimic wood grain, corn kernels, pine cone or walnuts. In this regard, the shape of the housing 20 may be selected to match the texture, so that the overall container resembles an object such as a pine cone, a walnut, or any of various types of seeds.

Figure 4:
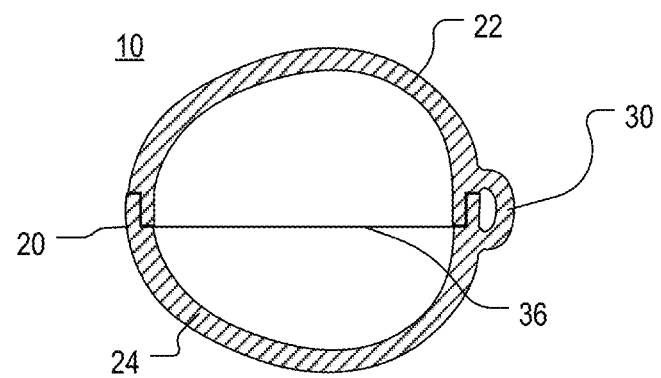
FIG. 4 is a side cross-sectional view of the edible pet medicine container of FIG. 2.
Figure 5:
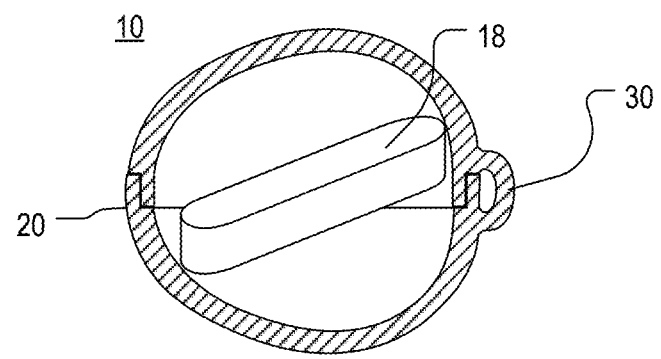
FIG. 5 is a side cross-sectional view of the edible pet medicine container of FIG. 2, shown with a pill disposed inside.

FIG. 4 is a side cross-sectional view of the edible pet medicine container 10 of FIG. 2. As shown therein, the two halves 22,24 are designed to be interlocked or otherwise coupled together so as to provide a closed, sealed or semi-sealed interior in which medicines, vitamins, or other materials may be filled, loaded or otherwise disposed for ingestion by an animal. For example, FIG. 5 is a side cross-sectional view of the edible pet medicine container 10 of FIG. 2, shown with a pill 18 disposed inside. Such an interlock or coupling advantageously prevents or discourages the container 10 from being opened while it is still in the animal's mouth (i.e., before it has been swallowed). It advantageously also serves to deter the animal from eating only the container 10 and spitting out the pill or medicine contained inside.

Figure 6:
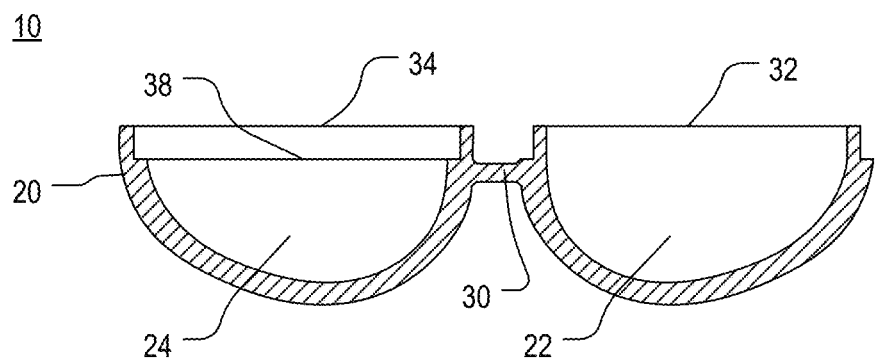
FIG. 6 is a side cross-sectional view of the edible pet medicine container of FIG. 4, shown in an open configuration.
Figure 7:
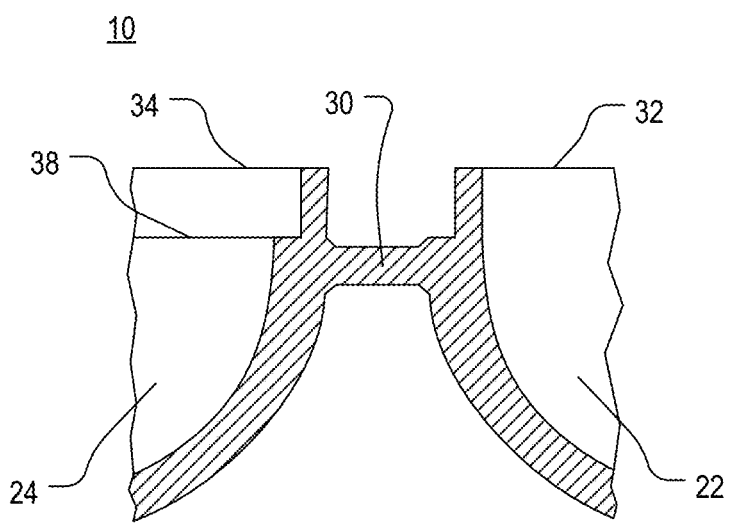
FIG. 7 is an enlarged, fragmentary side cross-sectional view of the edible pet medicine container of FIG. 6.
Figure 8:
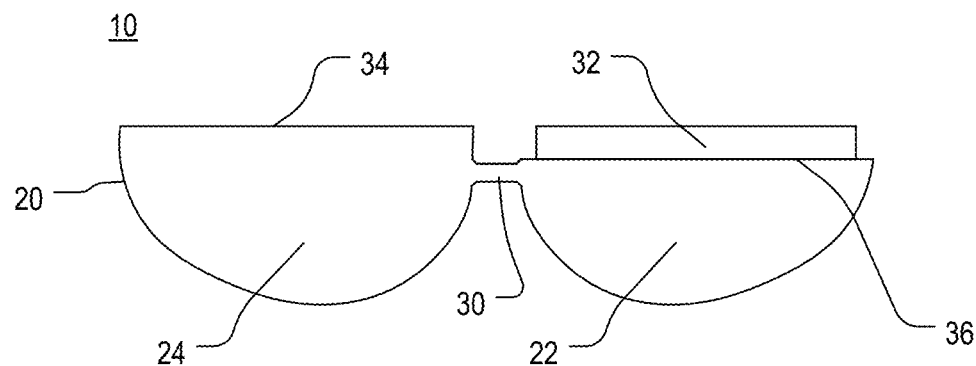
FIG. 8 is a side view of the edible pet medicine container of FIG. 2, shown in a fully open configuration.

A variety of structures may be used to interlock or otherwise couple the two halves 22,24 together. The connection established between the two halves 22,24 is preferably strong enough to maintain the two halves 22,24 in the closed configuration until the container 10 is safely placed in the mouth of the animal 14, and more preferably is strong enough to maintain the two halves 22,24 in the closed configuration until the animal 14 swallows the container 10. One set of structures achieving such a connection is illustrated in FIGS. 4-8, wherein FIG. 6 is a side cross-sectional view of the edible pet medicine container 10 of FIG. 4, shown in an open configuration; FIG. 7 is an enlarged, fragmentary side cross-sectional view of the edible pet medicine container 10 of FIG. 6; and FIG. 8 is a side view of the edible pet medicine container 10 of FIG. 2, shown in a fully open configuration. As shown therein, a rim 32 of the upper half 22 is shaped and sized so as to fit within a rim 34 of the lower half 24 when the two halves 22,24 are manipulated from the open configuration to the closed configuration. When fully closed, the rim 32 of the upper half 22 is seated on a ledge 38 within the rim 34 of the lower half 24, and the rim 34 of the lower half 24 is seated against a ledge 36 around the rim 32 of the upper half 22. The respective rims and ledges are thereby coupled together and retained in place via snap fit, friction fit, or the like.

The hinge or tether 30 permits the two halves 22,24 to be separated but kept close together so as to avoid dropping, losing or misplacing one of the halves while manipulating the other one. In at least some embodiments, the hinge may also provide assistance in holding the two halves together when placed in the closed configuration, and/or the hinge may also provide assistance in guiding the two halves together when manipulating the halves from the open configuration into the closed configuration. In at least some embodiments, the hinge or tether 30 is a living hinge that is flexible enough to provide a hinge function without degrading while the medicine or other ingestible is being loaded into the container 10 and administered to the animal 14.

In at least some embodiments, the container 10, including the housing halves 22,24 and the hinge or tether 30, is constructed from an edible base, such as a potato-based food material. The edible base is produced in the form of a hard or semi-hard shell structure created from a mixture. An appropriate mixture may be created and molded or otherwise formed into the desired shape and baked or allowed to dry according to conventional food preparation processes. The shell structure can be made via various high-volume food manufacturing processes such as molding, injection molding, stamping and the like. The hinge or tether 30 may be formed as part of the housing 20 or may be formed separately and added to the hinge halves 22,24. Additives, including preservatives, seasonings, and flavorings, may be added to the mixture, surface-coated onto the hardened shell, or the like. In one particular embodiment, the housing 20 is naturally or artificially bacon-flavored, beef flavored or chicken flavored.

Figure 9:
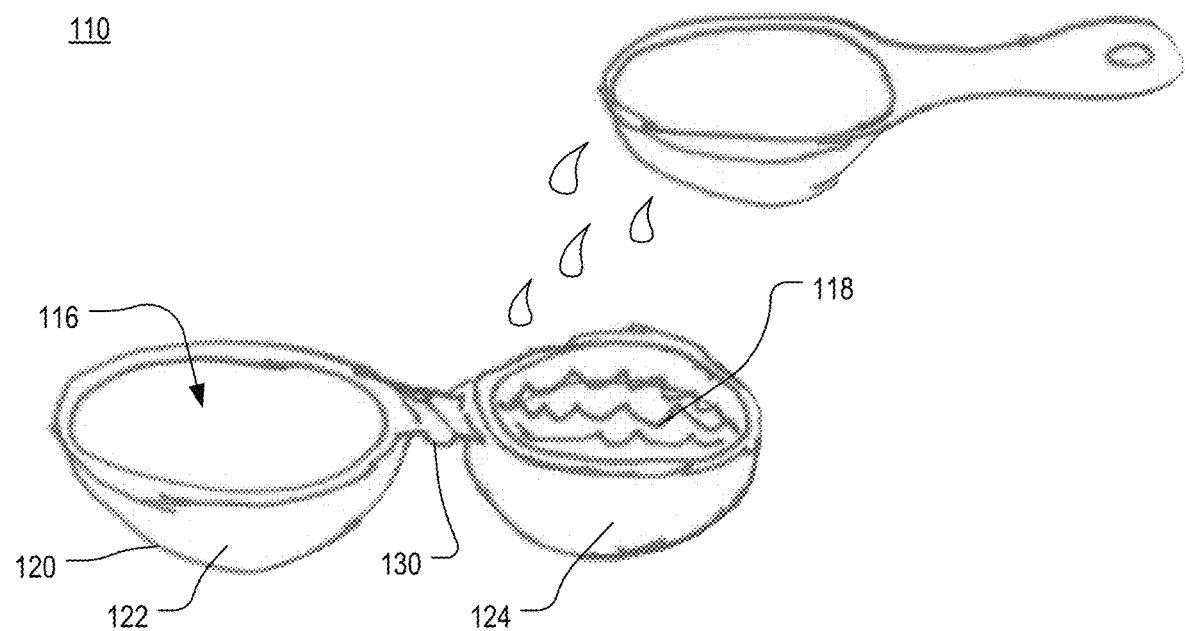
FIG. 9 is a side perspective view of an alternative edible pet medicine container, in accordance with one or more preferred embodiments of the present invention, shown being loaded with a medicine or other ingestible in liquid form.
Figure 10:
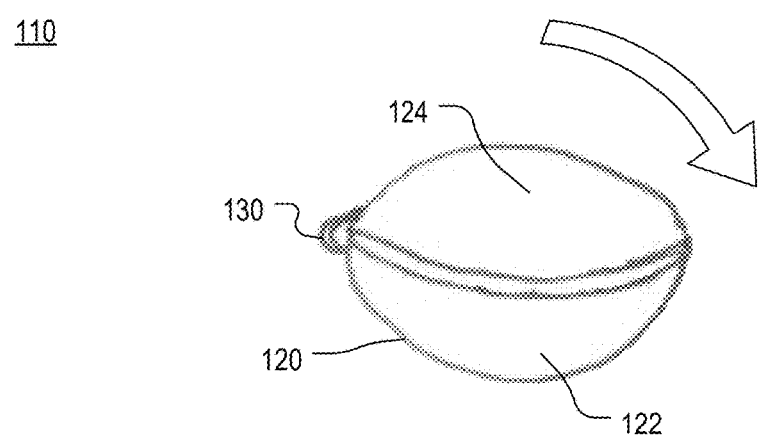
FIG. 10 is a side perspective view of the edible pet medicine container of FIG. 9, shown being closed.

As noted previously, the container 10 may preferably accept medicines and other animal-edible materials in various forms, including pill or other solid form, powder or granular form, liquid form, gel form, paste form, and the like. For example, FIG. 5 illustrated the disposition of a single pill 18 within a container 10. As another example, FIG. 9 is a side perspective view of an alternative edible pet medicine container 110, in accordance with one or more preferred embodiments of the present invention, shown being loaded with a medicine 118 or other ingestible in liquid form, and FIG. 10 is a side perspective view of the edible pet medicine container 110 of FIG. 9, shown being closed. As shown in FIGS. 9 and 10, the container 110 includes a housing 120, defining an interior 116, and a hinge or tether 130. The housing 120 includes an upper shell 122 and a lower shell 124, which at least for convenience may be referred to herein as an upper half and a lower half. In some embodiments, the housing 120 and hinge or tether 130 are of similar construction to the housing 20 and hinge or tether 30 of FIGS. 1-8, but in at least some embodiments, the housing 120 may be designed to hold a liquid 118, without dripping or soaking through, for at least a period of time sufficient to facilitate filling the lower half 124 and safe placement of the container 110 the mouth of the animal 14. Preferably, however, the housing 120 is still able to dissolve quickly once the container 110 enters the animal's digestive tract. In FIG. 9, the container 110 is shown with an appropriate amount of a liquid medicine 118 being measured out and poured or dripped into at least one half 124 thereof, and in FIG. 10, the container 110 is shown being closed by rotating the upper half 122 up and over the top of the lower half 124, enclosing the liquid 118 therein.

Figure 11:
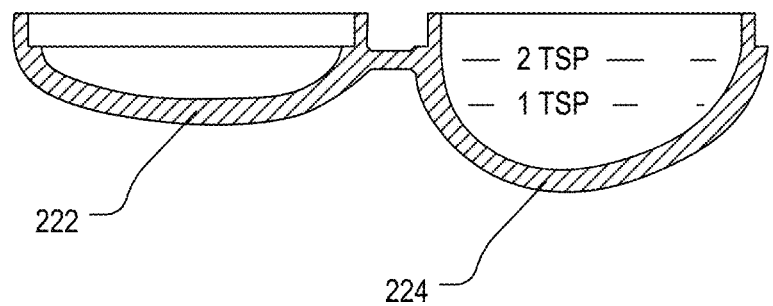
FIGS. 11 and 12 are side cross-sectional views of another alternative edible pet medicine container in accordance with one or more preferred embodiments of the present invention.
Figure 12:
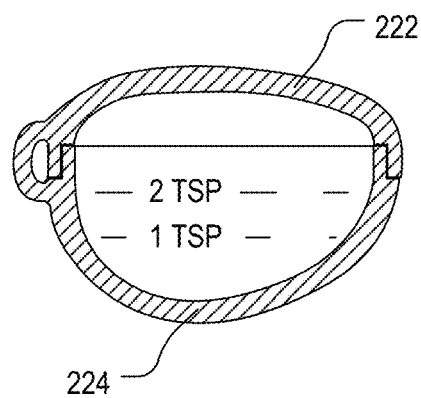

In at least some embodiments, one or both halves of a container have a volumetric capacity of a standard predetermined size so as to facilitate measurement of a desired volume of medicine or other ingestible material. For example, each half 122,124 of the container 110 of FIGS. 9 and 10 may be sized to receive a tablespoon of liquid, powder, granular, or soft solid material. In some embodiments, the two halves may not be equal in size, and each "half" is sized to accommodate a different predetermined volume. For example, FIGS. 11 and 12 are side cross-sectional views of another alternative edible pet medicine container 220 in accordance with one or more preferred embodiments of the present invention, wherein the left or top shell or half 222 has a capacity of one U.S. teaspoon while the right or bottom shell or half 224 has a capacity of one U.S. tablespoon. Furthermore, in some embodiments, one or both halves may include subdivided markings to make it possible to fill such half to a known quantity other than the full amount. For example, in FIGS. 11 and 12, the right or bottom half 224, which has a one tablespoon capacity, also has markings subdividing the overall capacity into one and two teaspoon increments. It will be appreciated, however, that other measurement increments and scales may additionally or alternatively be utilized without departing from the scope of the present invention. Such increments and scales may include, without limitation, milliliters, culinary units, weights (e.g., grams), and the like.

Figure 13:
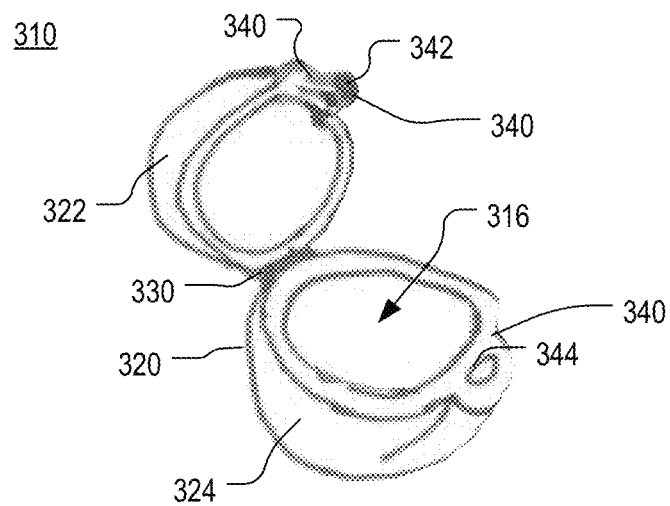
FIG. 13 is a perspective view of another alternative edible pet medicine container in accordance with one or more preferred embodiments of the present invention.
Figure 14:
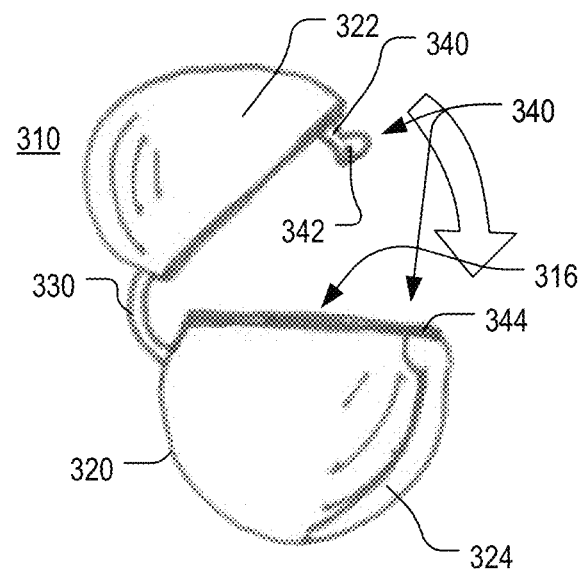
FIG. 14 is a side view of the edible pet medicine container of FIG. 6.

FIG. 13 is a perspective view of another alternative edible pet medicine container 310 in accordance with one or more preferred embodiments of the present invention, and FIG. 14 is a side view of the edible pet medicine container 310 of FIG. 6. As shown therein, the container 310 includes a housing 320, defining an interior 316, and a hinge or tether 330. The housing 320 includes an upper shell 322 and a lower shell 324, which at least for convenience may be referred to herein as an upper half and a lower half. The container 310 of FIG. 13 also includes a latch 340 for holding the two halves 322,324 together. The latch 340 includes a prong 342 on the upper half 322 and a receptacle 344 on the lower half 324, wherein the prong 342 may be forced into the receptacle 344 and retained there via snap fit, friction fit, or the like. Like the other portions of the container 310, the latch 340 is made from an edible base. It will be appreciated that other latch types may be substituted for the latch 340 shown in FIGS. 13 and 14. Such latch types may include, without limitation, rivets, one-way snaps, locking closures, and the like. Such a latch or locking mechanism advantageously prevents or discourages the container 310 from being opened while it is still in the animal's mouth (i.e., before it has been swallowed). It advantageously also serves to deter the animal 14 from eating only the container 310 and spitting out the pill or medicine contained inside.

Figure 15:
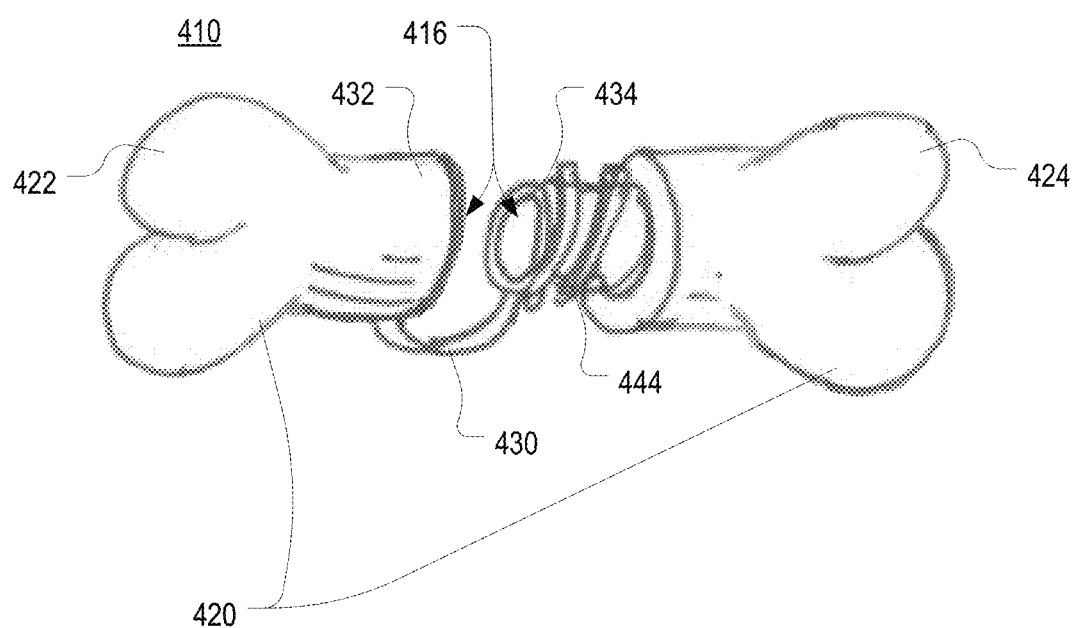
FIG. 15 is a perspective view of another alternative edible pet medicine container in accordance with one or more preferred embodiments of the present invention.

FIG. 15 is a perspective view of another alternative edible pet medicine container 410 in accordance with one or more preferred embodiments of the present invention. As shown therein, the container 410 takes the shape of a bone, although such shape need not be anatomically correct. Furthermore, the bone shape is only representative; the shape of the container may be of any desired shape, designed for the purposes herein. As shown in FIG. 15, the container 410 includes a housing 420, defining an interior 416, and a hinge or tether 430. The housing 420 includes a left portion 422 and a right portion 424, which at least for convenience may be referred to herein as a left half and a right half. In addition to having a unique shape, the container 410 of FIG. 15 also incorporates a threaded design for holding the two halves 422,424 together. In particular, a hollow male portion 434, having exterior threads 444, extends from the right half 424, while a female portion 432, having interior threads (not visible), forms a part of the left half 422. Once one or both of the halves 422,424 are filled with medicine or other ingestible material, they may be screwed together to retain the medicine inside. Such a threaded connection system advantageously prevents or discourages the container 410 from being opened while it is still in the animal's mouth (i.e., before it has been swallowed). It advantageously also serves to deter the animal 14 from eating only the container 410 and spitting out the pill or medicine contained inside. As with the other containers, all of the components of this container 410 may be made from an edible base.

Figure 16:
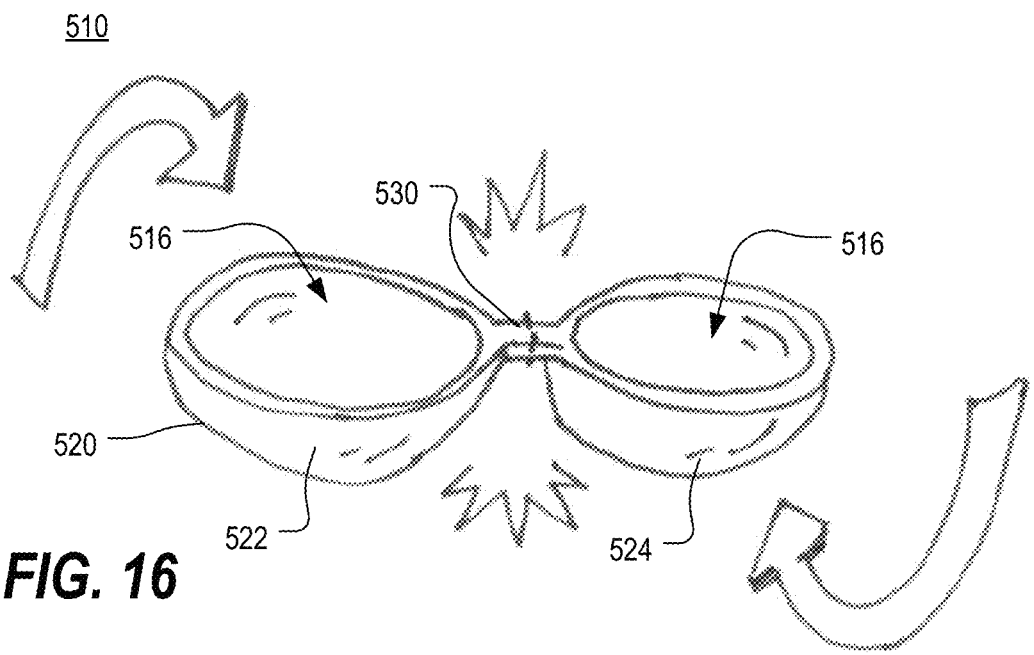
FIG. 16 is a perspective view of another alternative edible pet medicine container in accordance with one or more preferred embodiments of the present invention.
Figure 17:
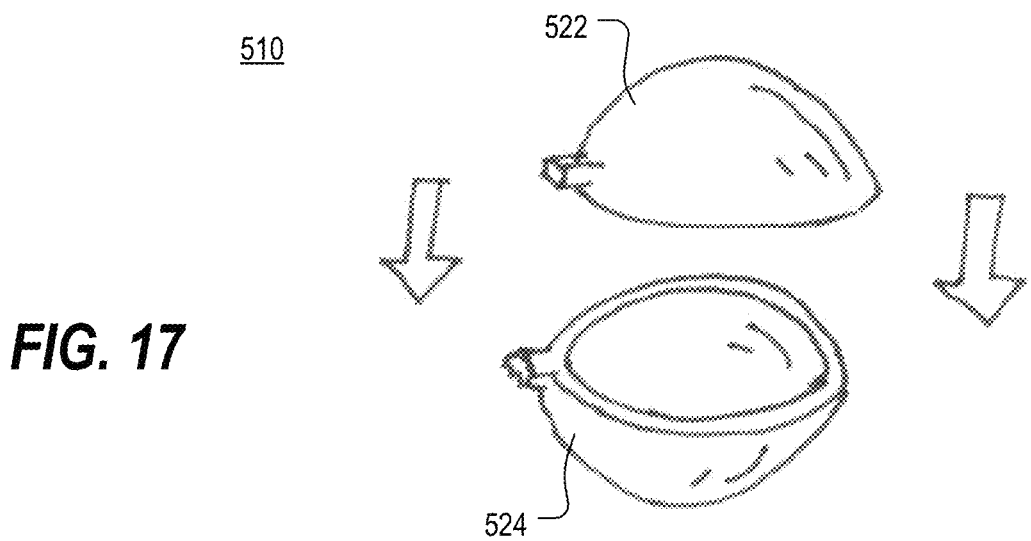
FIG. 17 is a perspective view of the halves of the edible pet medicine container being connected together to enclose a medicine or other ingestible material inside.
Figure 18:
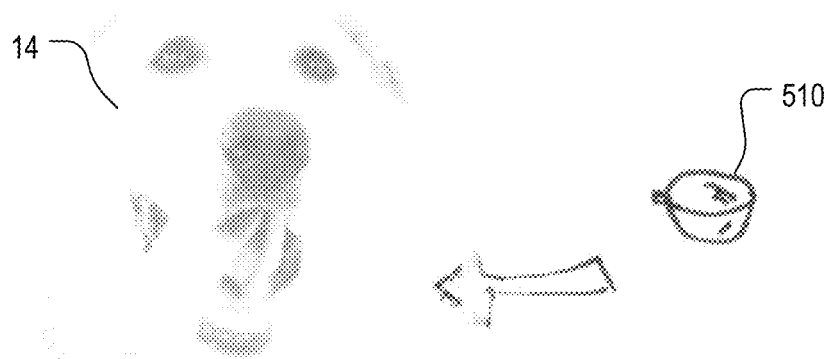
FIG. 18 is an illustration of the edible pet medicine container of FIG. 17 being fed to a canine.

FIG. 16 is a perspective view of another alternative edible pet medicine container 510 in accordance with one or more preferred embodiments of the present invention. As shown therein, the container 510 includes a housing 520, defining an interior 516, and a hinge or tether 530. The housing 520 includes an upper shell 522 and a lower shell 524, which at least for convenience may be referred to herein as an upper half and a lower half. The hinge or tether 530 of the container 510 of FIG. 16 takes the form of a neck or bridge that may or may not be flexible, but which may be easily broken to permit the upper half 522 to be manipulated into place on the lower half 524, as shown in FIG. 17, and the closed container 510, with the medicine inside it, may be fed or otherwise administered to the animal 14 as shown in FIG. 18. As with the other containers, all of the components of this container 510 may be made from an edible base. The two halves 522,524 may utilize any of the coupling or connection structures described herein, or may use other conventional coupling or connection structures to facilitate the halves 522,524 being coupled together.

Figure 19:
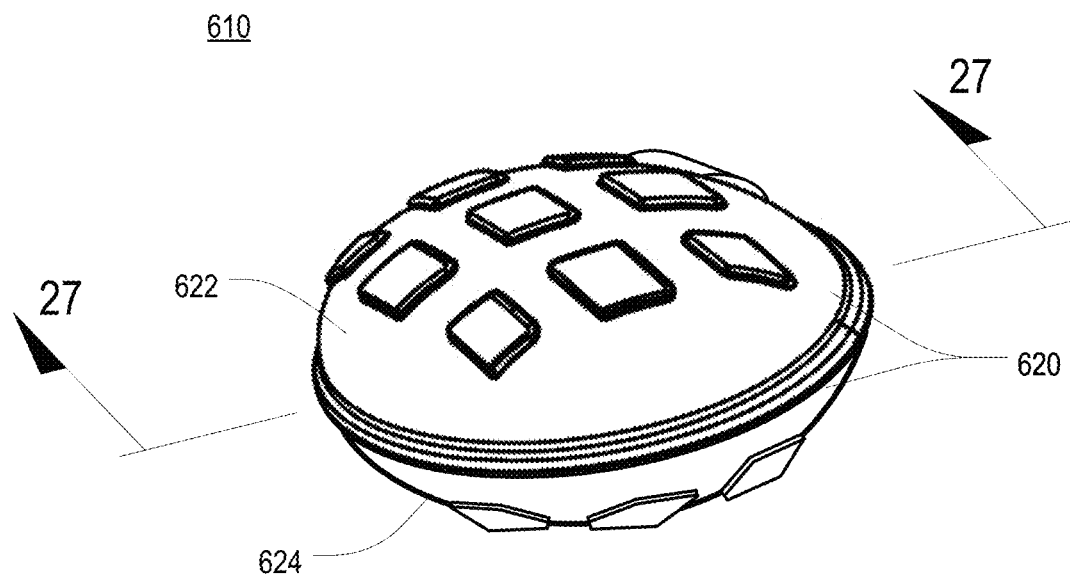
FIG. 19 is a perspective view of another alternative edible pet medicine container, shown in a closed state, in accordance with one or more preferred embodiments of the present invention.
Figure 20:
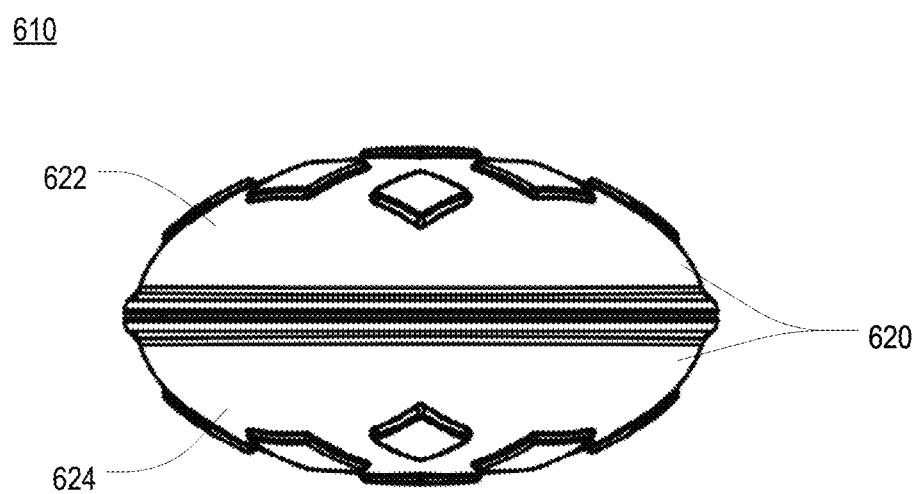
FIG. 20 is a side view of the edible pet medicine container of FIG. 19.
Figure 21:
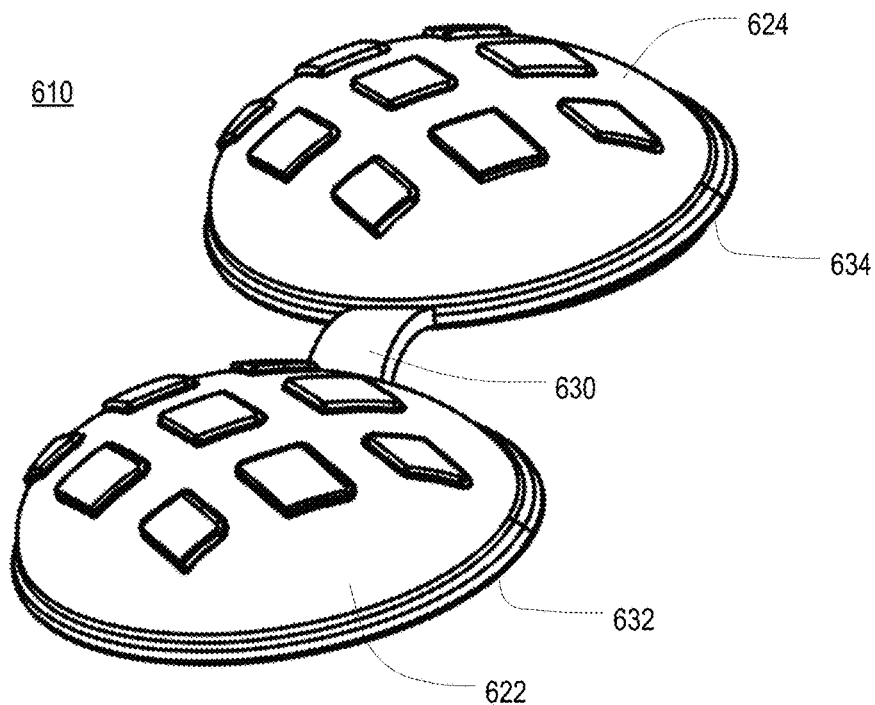
FIG. 21 is a bottom perspective view of the edible pet medicine container of FIG. 19, shown in an open state.
Figure 22:
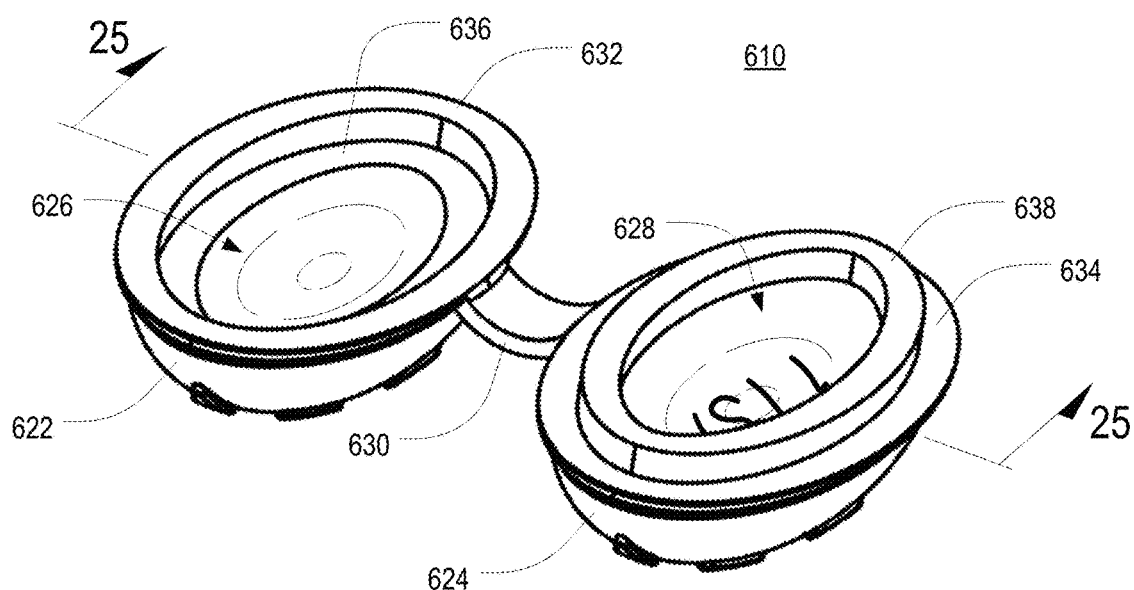
FIG. 22 is a top perspective view of the edible pet medicine container of FIG. 21, showing the interior thereof.
Figure 23:
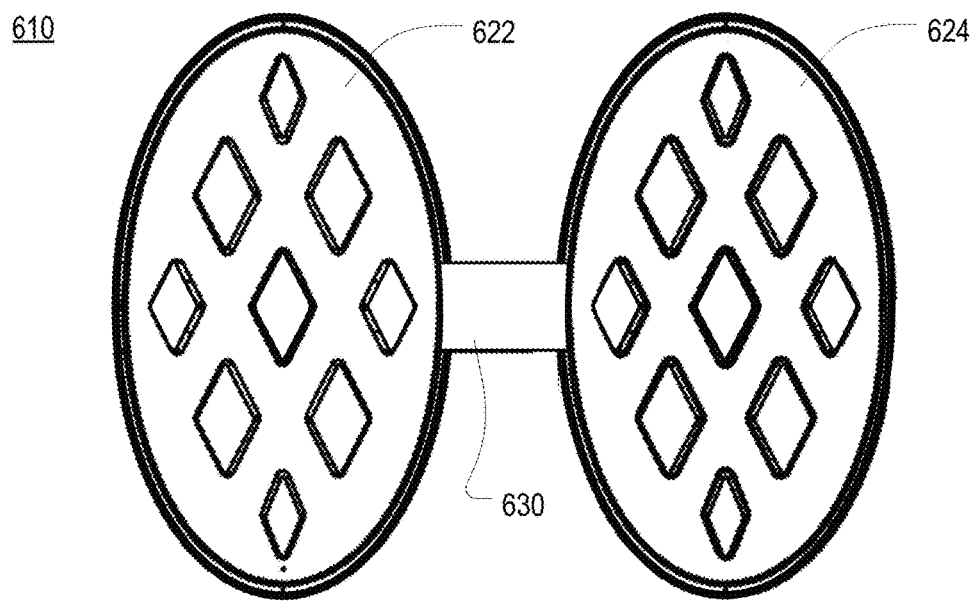
FIG. 23 is a bottom view of the edible pet medicine container of FIG. 21.
Figure 24:
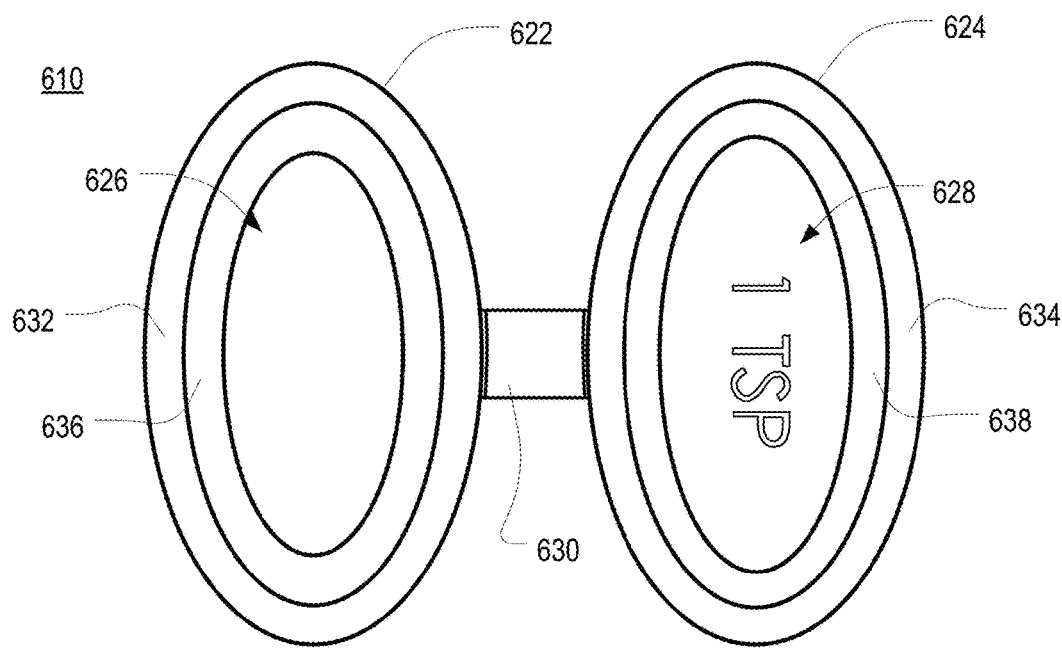
FIG. 24 is a top view of the edible pet medicine container of FIG. 21.

FIGS. 19 and 20 are a perspective view and a side view, respectively, of another alternative edible pet medicine container 610, shown in a closed state, in accordance with one or more preferred embodiments of the present invention; FIGS. 21 and 22 are a bottom perspective view and top perspective view, respectively, of the edible pet medicine container 610 of FIG. 19, shown in an open state; and FIGS. 23 and 24 are a bottom view and a top view, respectively, of the edible pet medicine container 610 of FIG. 21. As shown therein, the container 610 includes a housing 620, defining an interior 616, and a hinge or tether 630. The housing 620 includes an upper shell 622 and a lower shell 624, which at least for convenience may be referred to herein as an upper half and a lower half. As perhaps best illustrated in FIG. 22, the open face of each half 622,624 has a respective peripheral ledge 632,634 and a central hollow 626,628. Surrounding the central hollow 626 of the upper half 622, but interior from the peripheral ledge 632, is a recessed ledge 636, while surrounding the central hollow 628 of the lower half 624, but interior from the peripheral ledge 634, is a standing wall or higher-level ledge 638. The various ledges are shaped and sized to fit together as described below.

Figure 25:
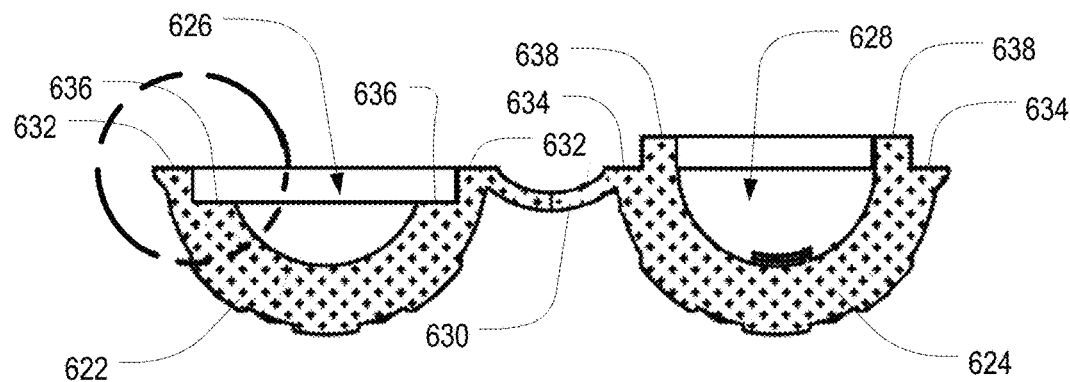
FIG. 25 is an end cross-sectional view of the edible pet medicine container of FIG. 22, taken along line 25-25.
Figure 26:
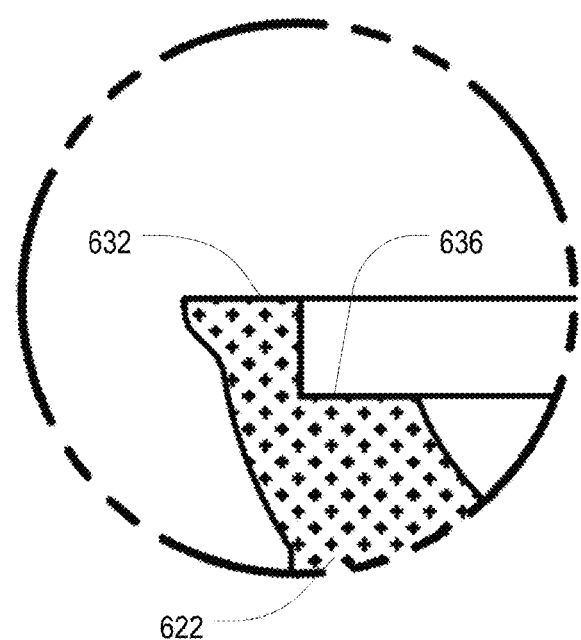
FIG. 26 is an enlarged fragmentary portion of the edible pet medicine container of FIG. 25.
Figure 27:
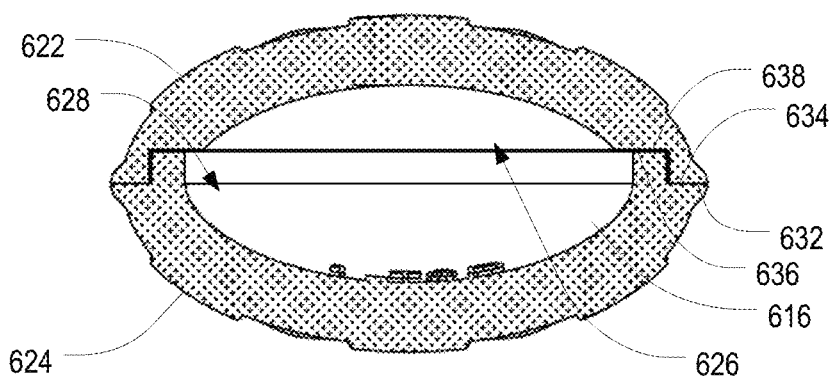
FIG. 27 is a side cross-sectional view of the edible pet medicine container of FIG. 19, taken along line 27-27.

FIG. 25 is an end cross-sectional view of the edible pet medicine container 610 of FIG. 22, taken along line 25-25; FIG. 26 is an enlarged fragmentary portion of the edible pet medicine container 610 of FIG. 25. The various ledges may be seen more clearly in FIG. 25, with some additional detail visible in FIG. 26. The two halves 622,624 may be fit together as shown in FIG. 27, which is a side cross-sectional view of the edible pet medicine container 610 of FIG. 19, taken along line 27-27. As shown therein, the standing wall or higher-level ledge 638 of the lower half 624 fits neatly into the recessed ledge 636 on the upper half 622, with the peripheral ledges 632,634 meeting one another. In this closed state, the central hollows 626,628 together form an interior 616.

Figure 28:
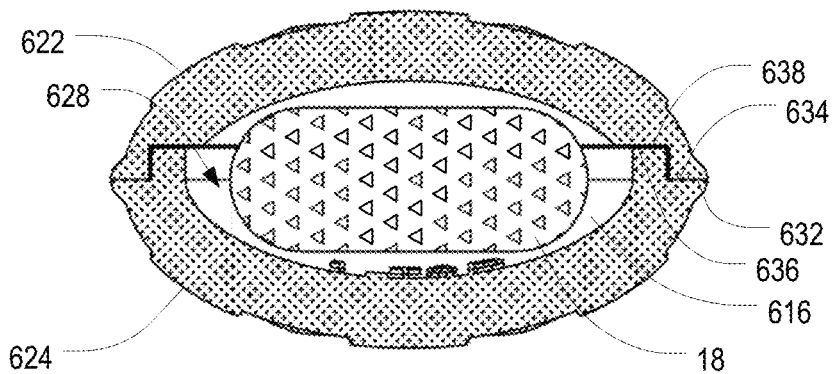
FIG. 28 is a side cross-sectional view of the edible pet medicine container of FIG. 27, shown with a pill loaded inside.

Due to the slightly flexible nature of the material from which the two halves 622,624 are made, the respective ledges are thereby coupled together and retained in place via friction fit, thereby providing a closed and sealed or semi-sealed interior in which medicines, vitamins, or other materials may be filled, loaded or otherwise disposed for ingestion by an animal 14. For example, FIG. 28 is a side cross-sectional view of the edible pet medicine container 610 of FIG. 27, shown with a pill 18 loaded inside. Such an interlock or coupling advantageously prevents or discourages the container 610 from being opened while it is still in the animal's mouth (i.e., before it has been swallowed). It advantageously also serves to deter the animal 14 from eating only the container 610 and spitting out the pill or medicine contained inside.

Notably, the peripheral ledges 632,634 of the upper and lower halves 622,624 are each flared outward relative to the rest of the body of the respective shell 622,624. This may perhaps be best seen in the profile views shown in FIGS. 20 and 25-28. Such flaring provides additional surface area for the ledges 632,634 and thus additional areas of contact (and perhaps better sealing) between such ledges, provides additional thickness for the walls of the shells 622,624 and thus additional width or thickness (and greater strength) to the various ledges, and provides additional contouring (and thus makes the exterior shape less artificial, more organic, and more appealing to a target animal) to the exterior of the container 610.

Because the two halves 622,624 are of slightly different design (e.g., the upper half 622 has a recessed ledge 636, while the lower half 624 has a standing ledge 638), it is necessary for each container 610 to utilize one upper half 622 and one lower half 624. The hinge 630 helps the user 12 avoid fumbling for a pair of matching halves 622,624 by clearly linking together one upper half 622 and one lower half 624. The hinge 630, as well as the two halves 622,624, may be made of materials similar to those of other halves and hinges or tethers described herein. Further, because the two halves 622,624 create a sealed or semi-sealed interior 616 when coupled together, this container 610 may be utilized to hold a liquid, such as a liquid medicine, in a manner similar to that of the container 110 of FIGS. 9 and 10. Furthermore, at least one half (such as the lower half 624 as perhaps best shown in FIG. 24) may be labeled with the effective volume of the container 610 for purposes of facilitating precise dosing. This may be accomplished, for example, by embossing, stamping, or otherwise marking one or both of the halves 622,624 on their interior or exterior. In the embodiment of FIGS. 19-28, the interior of the lower half 624 has been embossed with the label "1 TSP" to indicate that the central hollow of the lower shell 624 has a volume of one teaspoon.

Figure 29:
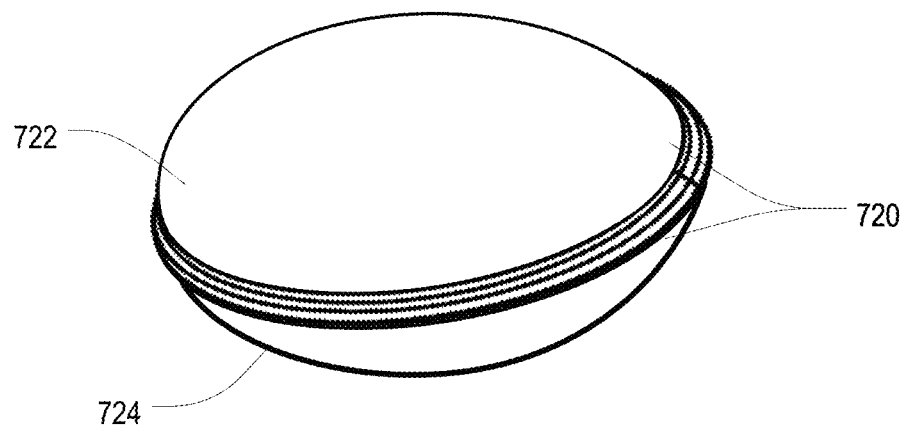
FIG. 29 is a perspective view of another alternative edible pet medicine container, shown in a closed state, in accordance with one or more preferred embodiments of the present invention.
Figure 30:
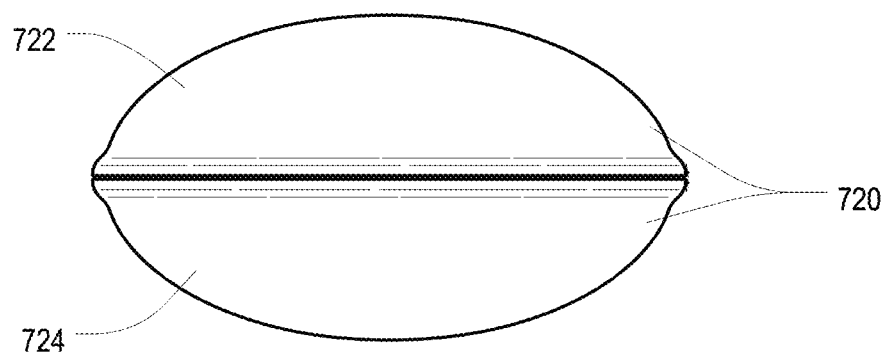
FIG. 30 is a side view of the edible pet medicine container of FIG. 29.
Figure 31:
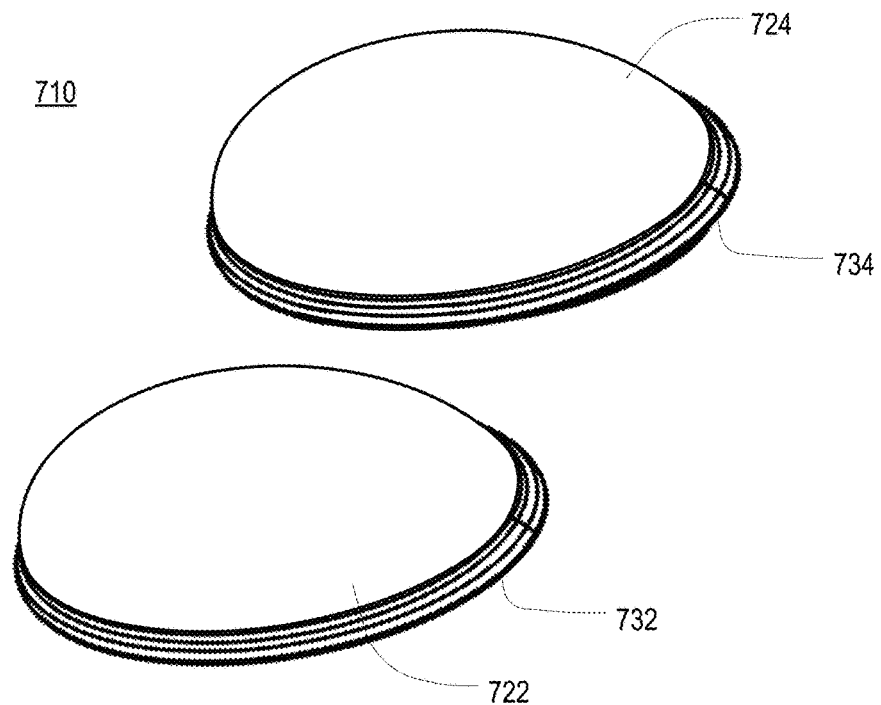
FIG. 31 is a bottom perspective view of the edible pet medicine container of FIG. 29, shown in an open state.
Figure 32:
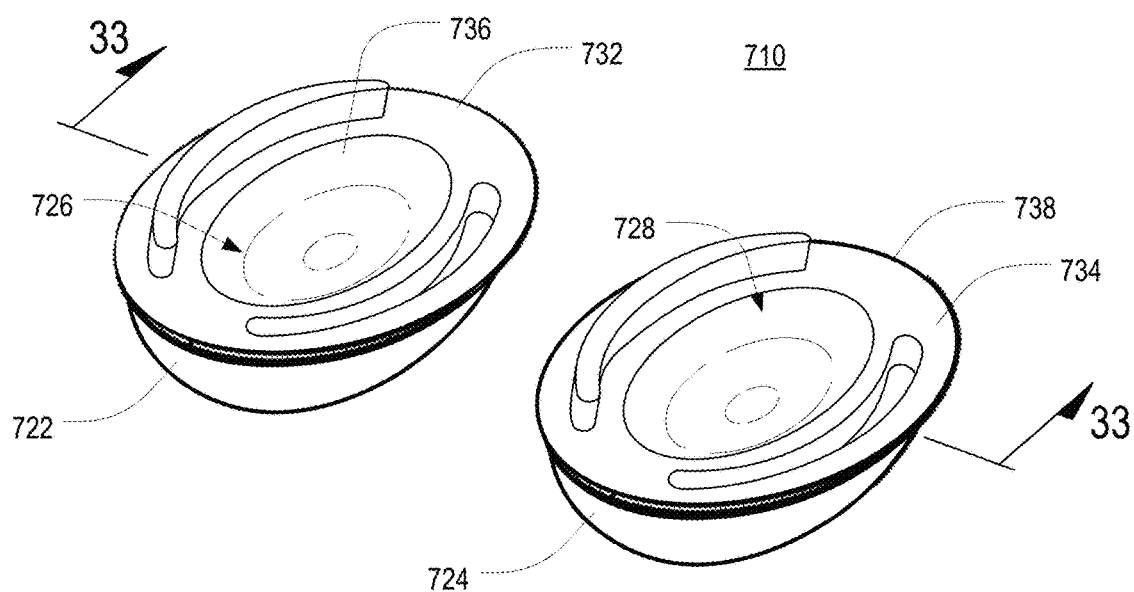
FIG. 32 is a top perspective view of the edible pet medicine container of FIG. 31, showing the interior thereof.
Figure 33:
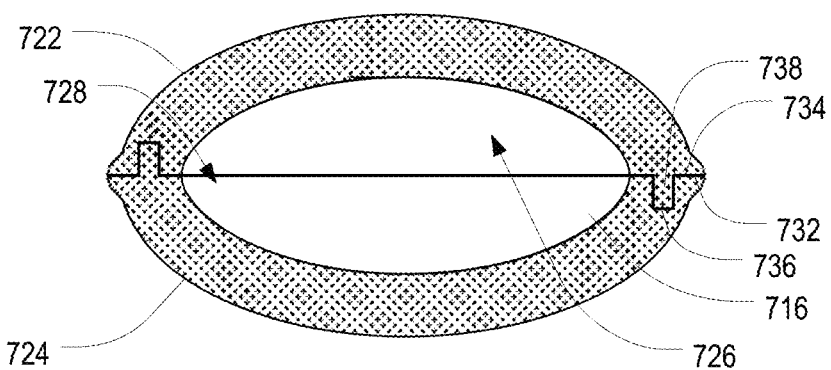
FIG. 33 is a side cross-sectional view of the edible pet medicine container of FIG. 29, taken along line 33-33.

FIGS. 29 and 30 are a perspective view and a side view, respectively, of another alternative edible pet medicine container 710, shown in a closed state, in accordance with one or more preferred embodiments of the present invention; and FIGS. 31 and 32 are a bottom perspective view and a top perspective view, respectively, of the edible pet medicine container 710 of FIG. 29, shown in an open state. As shown therein, the container 710 includes a housing 720, defining an interior 716, that includes an upper shell 722 and a lower shell 724, which at least for convenience may be referred to herein as an upper half and a lower half. As perhaps best illustrated in FIG. 32, the open face of each half 722,724 has a respective peripheral ledge 732,734 and a central hollow 726,728. A recessed ledge or slot 736 is arranged in the peripheral ledge 732,734 along one lateral side of each half 722,724, while a corresponding standing wall or ledge 738 is disposed on the peripheral ledge 732,734 along the opposite lateral side of each half 722,724. The cross-section of the standing wall or ledge 738 is similar to that of the recessed ledge or slot 736 such that the standing wall or ledge 738 of the upper half 722 may be fit snugly inside the recessed ledge or slot 736 of the lower half 724, and such that the standing wall or ledge 738 of the lower half 724 may be fit snugly inside the recessed ledge or slot 736 of the upper half 722. In this regard, FIG. 33 is an end cross-sectional view of the edible pet medicine container 710 of FIG. 32, taken along line 33-33. As shown therein, the standing wall or ledges 738 fit neatly into the recessed ledges or slots 736 with the peripheral ledges 732,734 meeting one another. In this closed state, the central hollows 726,728 together form an interior 716.

Figure 34:
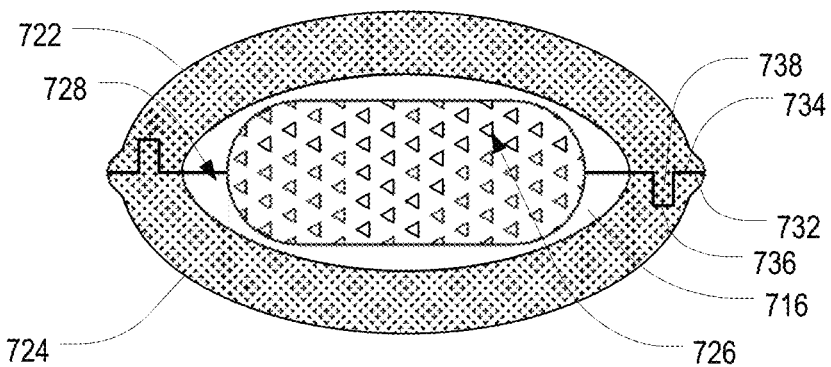
FIG. 34 is a side cross-sectional view of the edible pet medicine container of FIG. 33, shown with a pill loaded inside.

Due to the slightly flexible nature of the material from which the two halves 722,724 are made, the respective ledges are thereby coupled together and retained in place via friction fit, thereby providing a closed and sealed or semi-sealed interior in which medicines, vitamins, or other materials may be filled, loaded or otherwise disposed for ingestion by an animal 14. For example, FIG. 34 is a side cross-sectional view of the edible pet medicine container 710 of FIG. 33, shown with a pill 18 loaded inside. Such an interlock or coupling advantageously prevents or discourages the container 710 from being opened while it is still in the animal's mouth (i.e., before it has been swallowed). It advantageously also serves to deter the animal 14 from eating only the container 710 and spitting out the pill or medicine contained inside.

Notably, the peripheral ledges 732,734 of the upper and lower halves 722,724 are each flared outward relative to the rest of the body of the respective shell 722,724. This may perhaps be best seen in the profile views shown in FIGS. 29, 33, and 34. Such flaring provides additional surface area for the ledges 732,734 and thus additional areas of contact (and perhaps better sealing) between such ledges, provides additional thickness for the walls of the shells 722,724 and thus additional width or thickness (and greater strength) to the various ledges, and provides additional contouring (and thus makes the exterior shape less artificial, more organic, and more appealing to a target animal) to the exterior of the container 710.

Because the two halves 722,724 are of identical design (e.g., the upper half 722 has a recessed ledge 736 along one side and a standing wall 738 along the other side, and the lower half 724 likewise has a recessed ledge 736 along one side and a standing wall 738 along the other side), it is not necessary to distinguish upper halves 722 from lower halves 724. Thus, although it may be useful for other purposes, it is not necessary to tether the upper half 722 to the lower half 724 to make it easier for a user 12 to find matching halves 722,724.

In at least some embodiments, because the two halves 722,724 create a semi-sealed interior 716 when coupled together, this container 710 may be utilized to hold a liquid, such as a liquid medicine, in a manner similar to that of the container 110 of FIGS. 9 and 10.

Figure 35:
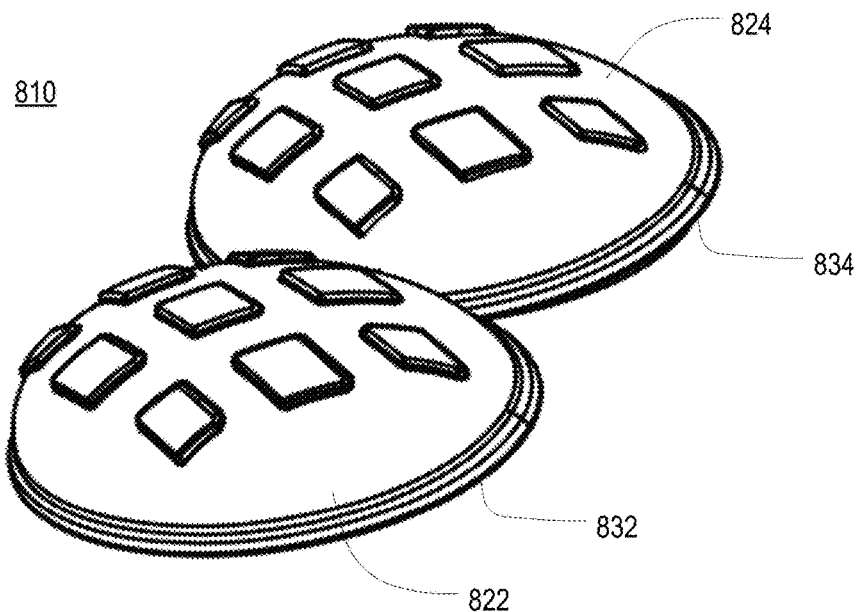
FIG. 35 is a bottom perspective view of another alternative edible pet medicine container, shown in an open state, in accordance with one or more preferred embodiments of the present invention.
Figure 36:
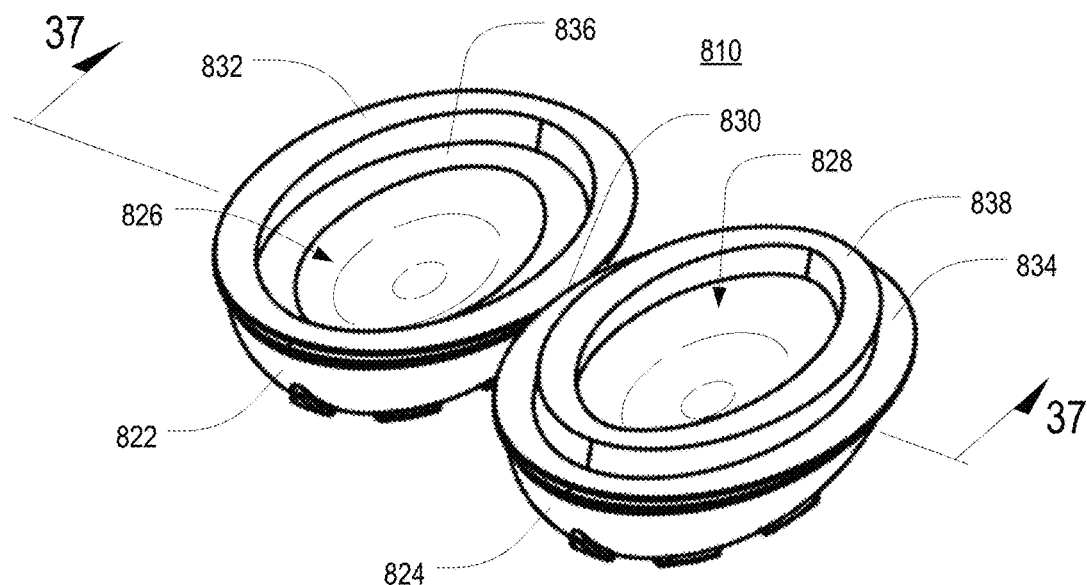
FIG. 36 is a top perspective view of the edible pet medicine container of FIG. 35.
Figure 37:
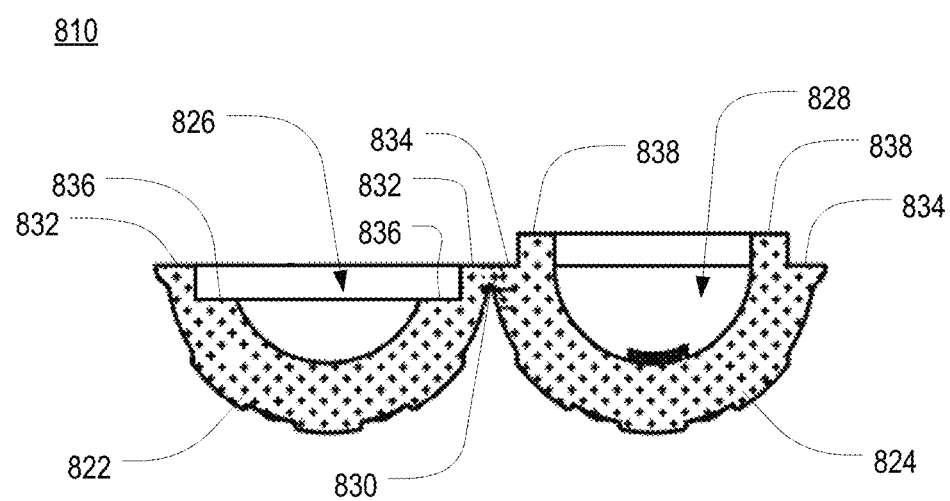
FIG. 37 is an end cross-sectional view of the edible pet medicine container of FIG. 36, taken along line 37-37.

FIGS. 35 and 36 are a bottom perspective view and top perspective view, respectively, of another alternative edible pet medicine container 810, shown in an open state, in accordance with one or more preferred embodiments of the present invention; and FIG. 37 is an end cross-sectional view of the edible pet medicine container 810 of FIG. 36, taken along line 37-37.

As shown therein, the container 810 includes a housing 820, defining an interior 816, and a connective structure 830. The housing 820 includes an upper shell 822 and a lower shell 824, which at least for convenience may be referred to herein as an upper half and a lower half. As perhaps best illustrated in FIG. 36, the open face of each half 822,824 has a respective peripheral ledge 832,834 and a central hollow 826,828. Surrounding the central hollow 826 of the upper half 822, but interior from the peripheral ledge 832, is a recessed ledge 836, while surrounding the central hollow 828 of the lower half 824, but interior from the peripheral ledge 834, is a standing wall or higher-level ledge 838. The various ledges are shaped and sized to fit together as described below.

The construction of this container 810 is very similar to that of the container of FIGS. 19-28 except that the two halves 822,824 may be initially provided in a connected state, wherein an edge of the upper half 822 is integrally attached directly to an edge of the lower half 824 via the connective structure 830 rather than a more clearly defined hinge or tether. This connective structure 830 may be a rigid or semi-rigid connection that may easily be snapped and/or broken by a user 12 to enable the two halves 822,824 to be fitted together in a manner similar to that shown in FIG. 27. In this state, the standing wall or higher-level ledge 838 of the lower half 824 fits neatly into the recessed ledge 836 on the upper half 822, with the peripheral ledges 832,834 meeting one another. In this closed state, the central hollows 826,828 together form an interior.

Due to the slightly flexible nature of the material from which the two halves 822,824 are made, the respective ledges are thereby coupled together and retained in place via friction fit, thereby providing a closed and sealed or semi-sealed interior in which medicines, vitamins, or other materials may be filled, loaded or otherwise disposed for ingestion by an animal 14. Such an interlock or coupling advantageously prevents or discourages the container 810 from being opened while it is still in the animal's mouth (i.e., before it has been swallowed). It advantageously also serves to deter the animal 14 from eating only the container 810 and spitting out the pill or medicine contained inside.

Notably, the peripheral ledges 832,834 of the upper and lower halves 822,824 are each flared outward relative to the rest of the body of the respective shell 822,824. Such flaring provides additional surface area for the ledges 832,834 and thus additional areas of contact (and perhaps better sealing) between such ledges, provides additional thickness for the walls of the shells 822,824 and thus additional width or thickness (and greater strength) to the various ledges, and provides additional contouring (and thus makes the exterior shape less artificial, more organic, and more appealing to a target animal) to the exterior of the container 810.

Because the two halves 822,824 are of slightly different design (e.g., the upper half 822 has a recessed ledge 836, while the lower half 824 has a standing ledge 838), it is necessary for each container 810 to utilize one upper half 822 and one lower half 824. The structural connection 830 helps the user 12 avoid fumbling for a pair of matching halves 822,824 by clearly linking together one upper half 822 and one lower half 824. However, unlike the container 610 of FIGS. 19-28, this container 810 lacks a distinct hinge or tether structure, which may help avoid the creation of a sharp or otherwise uncomfortable edge or structure that might otherwise bother an animal 14 that consumes it. The structural connection 830, as well as the two halves 822,824, may be made of materials similar to those of other halves, hinges and tethers described herein. Further, because the two halves 822,824 create a sealed or semi-sealed interior when coupled together, this container 810 may be utilized to hold a liquid, such as a liquid medicine, in a manner similar to that of the container 110 of FIGS. 9 and 10. Furthermore, at least one half may be labeled with the effective volume of the container 810 for purposes of facilitating precise dosing.

Figure 38:
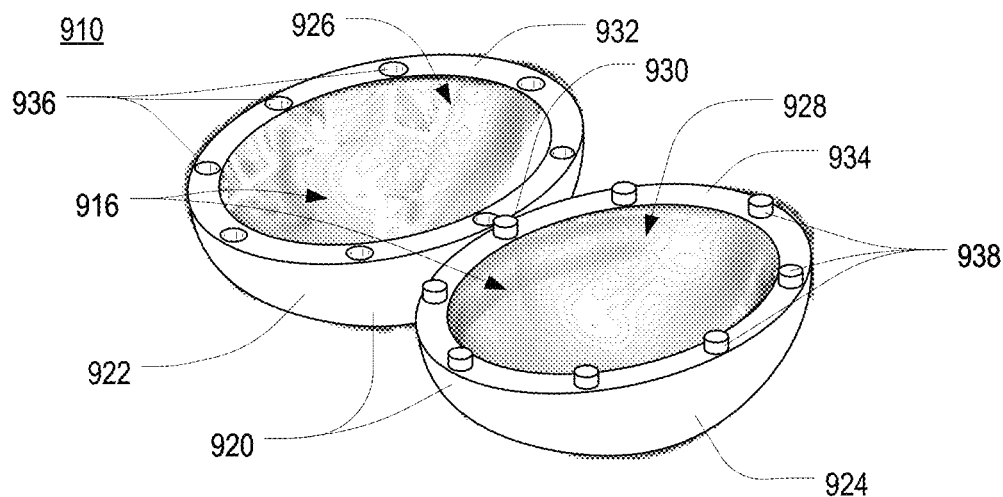
FIG. 38 is a top perspective view of another alternative edible pet medicine container, shown in an open state, in accordance with one or more preferred embodiments of the present invention.
Figure 39:
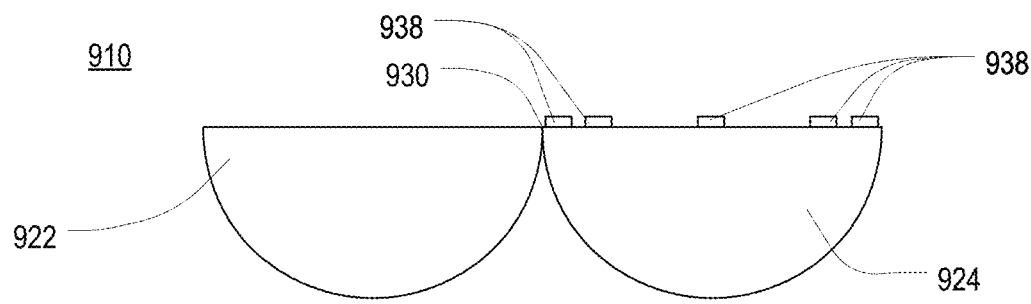
FIG. 39 is a side view of the edible pet medicine container of FIG. 38.
Figure 40:
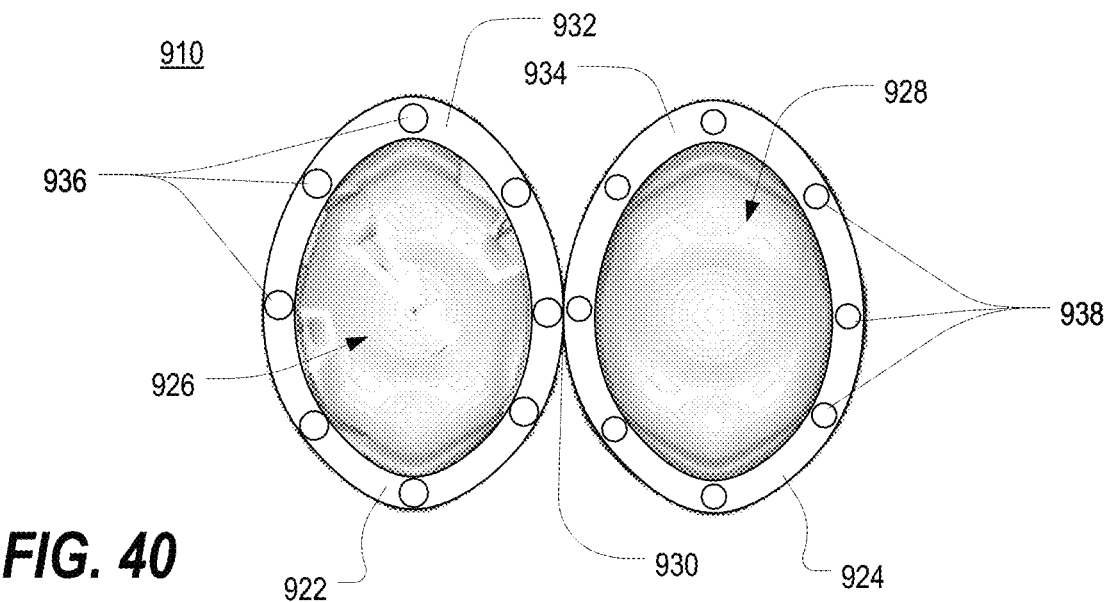
FIG. 40 is a top view of the edible pet medicine container of FIG. 38.

FIG. 38 is a top perspective view of another alternative edible pet medicine container 910, shown in an open state, in accordance with one or more preferred embodiments of the present invention, while FIGS. 39 and 40 are a side view and a top view, respectively, of the edible pet medicine container 910 of FIG. 38.

As shown therein, the container 910 includes a housing 920, defining an interior 916, and a connective structure 930. The housing 920 includes an upper shell 922 and a lower shell 924, which at least for convenience may be referred to herein as an upper half and a lower half. The open face of each half 922,924 has a respective peripheral ledge 932,934 and a central hollow 926,928. Spaced around the central hollow 926 of the upper half 922 are a series of cylindrical recesses (recessed ledges) 936 extending into the peripheral ledge 932, while surrounding the central hollow 928 of the lower half 924 are a series of cylindrical pegs (higher-level ledges) 938 extending or standing from the surface of the peripheral ledge 934. The various ledges are shaped and sized to fit together as described below.

Other than the arrangement of the ledges 936,938, the construction of this container 910 is very similar to that of the container 810 of FIGS. 35-37. The two halves 922,924 may be initially provided in a connected state, wherein an edge of the upper half 922 is integrally attached directly to an edge of the lower half 924 via the connective structure 930 rather than a more clearly defined hinge or tether. This connective structure 930 may be a rigid or semi-rigid connection that may easily be snapped and/or broken by a user 12 to enable the two halves 922,924 to be fitted together in a manner similar to that shown in FIG. 27. In this state, the pegs or higher-level ledges 938 of the lower half 924 fit neatly into the recesses or recessed ledges 936 in the upper half 922, with the peripheral ledges 932,934 meeting one another. In this closed state, the central hollows 926,928 together form an interior.

Due to the slightly flexible nature of the material from which the two halves 922,924 are made, the respective ledges are thereby coupled together and retained in place via friction fit, thereby providing a closed and sealed or semi-sealed interior in which medicines, vitamins, or other materials may be filled, loaded or otherwise disposed for ingestion by an animal 14. Such an interlock or coupling advantageously prevents or discourages the container 910 from being opened while it is still in the animal's mouth (i.e., before it has been swallowed). It advantageously also serves to deter the animal 14 from eating only the container 910 and spitting out the pill or medicine contained inside.

Notably, the cylindrical recesses and pegs 936,938 of the upper and lower halves 922,924 represent just one of a variety of interlocking features that may be utilized to couple and hold the upper and lower halves 922,924 together. A larger or smaller number of recesses and pegs 936,938 may be utilized, or the shape of the recesses and pegs 936,938 may be varied.

Because the two halves 922,924 are of slightly different design (e.g., the upper half 922 has a plurality of recesses or recessed ledges 936, while the lower half 924 has a plurality of pegs or standing ledges 938), it is necessary for each container 910 to utilize one upper half 922 and one lower half 924. The structural connection 930 helps the user 12 avoid fumbling for a pair of matching halves 922,924 by clearly linking together one upper half 922 and one lower half 924. However, unlike the container 610 of FIGS. 19-28, this container 910 lacks a distinct hinge or tether structure, which may help avoid the creation of a sharp or otherwise uncomfortable edge or structure that might otherwise bother an animal 14 that consumes it. The structural connection 930, as well as the two halves 922,924, may be made of materials similar to those of other halves, hinges and tethers described herein. Further, because the two halves 922,924 create a sealed or semi-sealed interior when coupled together, this container 910 may be utilized to hold a liquid, such as a liquid medicine, in a manner similar to that of the container 110 of FIGS. 9 and 10. Furthermore, at least one half may be labeled with the effective volume of the container 910 for purposes of facilitating precise dosing.

Figure 41:
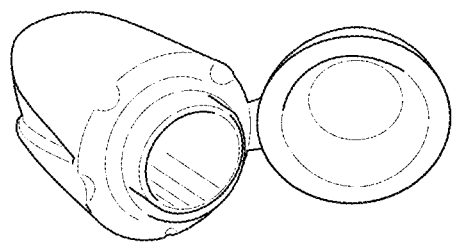
FIG. 41 is a perspective view of another alternative of the flexible, multi-function edible animal medicine container, shown in an open state, in accordance with one or more preferred embodiments of the present invention.
Figure 42:
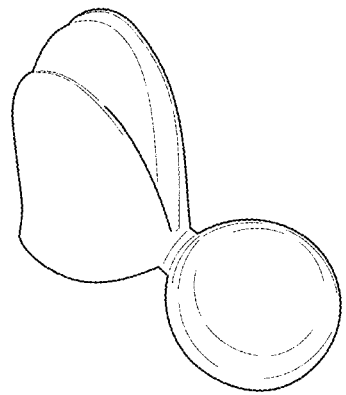
FIG. 42 is a top perspective view of the flexible multi-function edible animal medicine container of FIG. 41.
Figure 43:
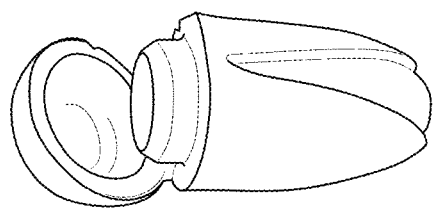
FIG. 43 is a side perspective view of the flexible multi-function edible animal medicine container of FIG. 41.
Figure 44:
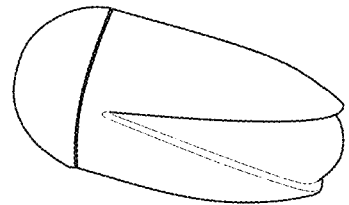
FIG. 44 is a perspective view of the flexible multi-function edible animal medicine container of FIG. 41, in a closed state.

FIGS. 41 and 42 are perspective views of another alternative edible pet medicine container, shown in an open state, in accordance with one or more preferred embodiments of the present invention; FIG. 43 is a perspective view of the edible pet medicine container of FIG. 41, shown in a partially closed state; and FIG. 44 is a perspective view of the edible pet medicine container of FIG. 41, shown in a fully closed state. As shown therein, the container includes a housing, defining an interior, and a hinge or tether. The housing includes an upper shell and a lower shell which are of different sizes. As perhaps best illustrated in FIG. 43, the open face of each shell has a respective peripheral ledge and a central hollow. Surrounding the central hollow of the upper (smaller) shell, but interior from the peripheral ledge, is a recessed ledge, while surrounding the central hollow of the lower (larger) half, but interior from the peripheral ledge, is a standing wall or higher-level ledge. The various ledges are shaped and sized to fit together as described below.

Because the two shells are of different design (e.g., the upper shell has a recessed ledge, while the lower shell has a standing ledge), it is necessary for each container to utilize one upper shell and one lower shell. The hinge helps the user 12 avoid fumbling for a pair of matching shells by clearly linking together one upper shell and one lower shell. The hinge, as well as the two shells, may be made of materials similar to those of other shells and hinges or tethers described herein. Further, because the two shells create a sealed or semi-sealed interior when coupled together, this container may be utilized to hold a liquid, such as a liquid medicine, in a manner similar to that of the container 110 of FIGS. 9 and 10.

Figure 45:
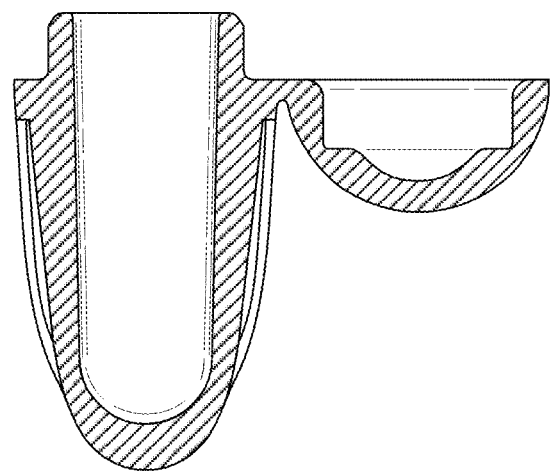
FIG. 45 is a side cross-sectional view of the edible pet medicine container of FIG. 41.
Figure 46:
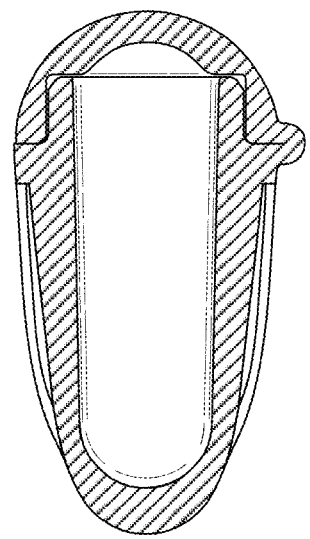
FIG. 46 is a side cross-sectional view of the edible pet medicine container of FIG. 44.
Figure 47:
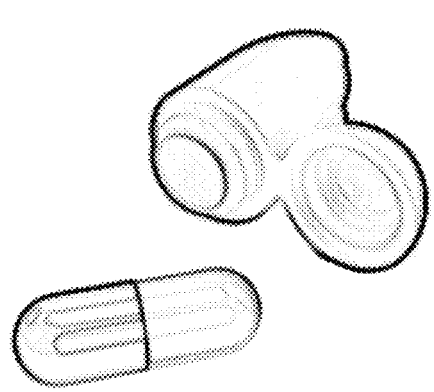
FIG. 47 is a perspective view of the flexible multi-function edible animal medicine container of FIG. 41 with a medicine capsule.

FIG. 45 is a side cross-sectional view of the edible pet medicine container of FIG. 41. The various ledges may be seen more clearly in FIG. 45. The two shells may be fit together as shown in FIG. 46, which is a side cross-sectional view of the edible pet medicine container of FIG. 44. As shown therein, the standing wall or higher-level ledge of the lower shelf fits neatly into the recessed ledge on the upper shell, with the peripheral ledges meeting one another. In this closed state, the central hollows together form an interior.

Due to the slightly flexible nature of the material from which the two halves are made, the respective ledges are thereby coupled together and retained in place via friction fit, thereby providing a closed and sealed or semi-sealed interior in which medicines, vitamins, or other materials may be filled, loaded or otherwise disposed for ingestion by an animal 14. For example, FIGS. 47 through 50 illustrate how to take a capsule medication and insert it into the edible pet medicine container of FIG. 41 and close it. Such an interlock or coupling advantageously prevents or discourages the container from being opened while it is still in the animal's mouth (i.e., before it has been swallowed). It advantageously also serves to deter the animal 14 from eating only the container and spitting out the pill or medicine contained inside.

Notably, when the pill is inserted, the exterior surfaces of the capsule may or may not friction fit to the interior surfaces of the edible container. In the instance where there is a friction fit, a suction grip force is also generated in the lower portion of the present invention in the vacuum chamber of the present invention. The vacuum chamber is formed when there is an air seal formed between the capsule exterior and the container's interior. The use of the vacuum chamber provides suction force on the capsule, so once inserted into the container, the capsule is held in place by the suction force of the vacuum chamber. Once the capsule is placed inside the present invention, the user may use the cap and close the container and lock it closed with a seal that is air tight so that no air or smells of the medicine inside the container escape, thus hiding the smell of the medicine from the animal.

Figure 51:
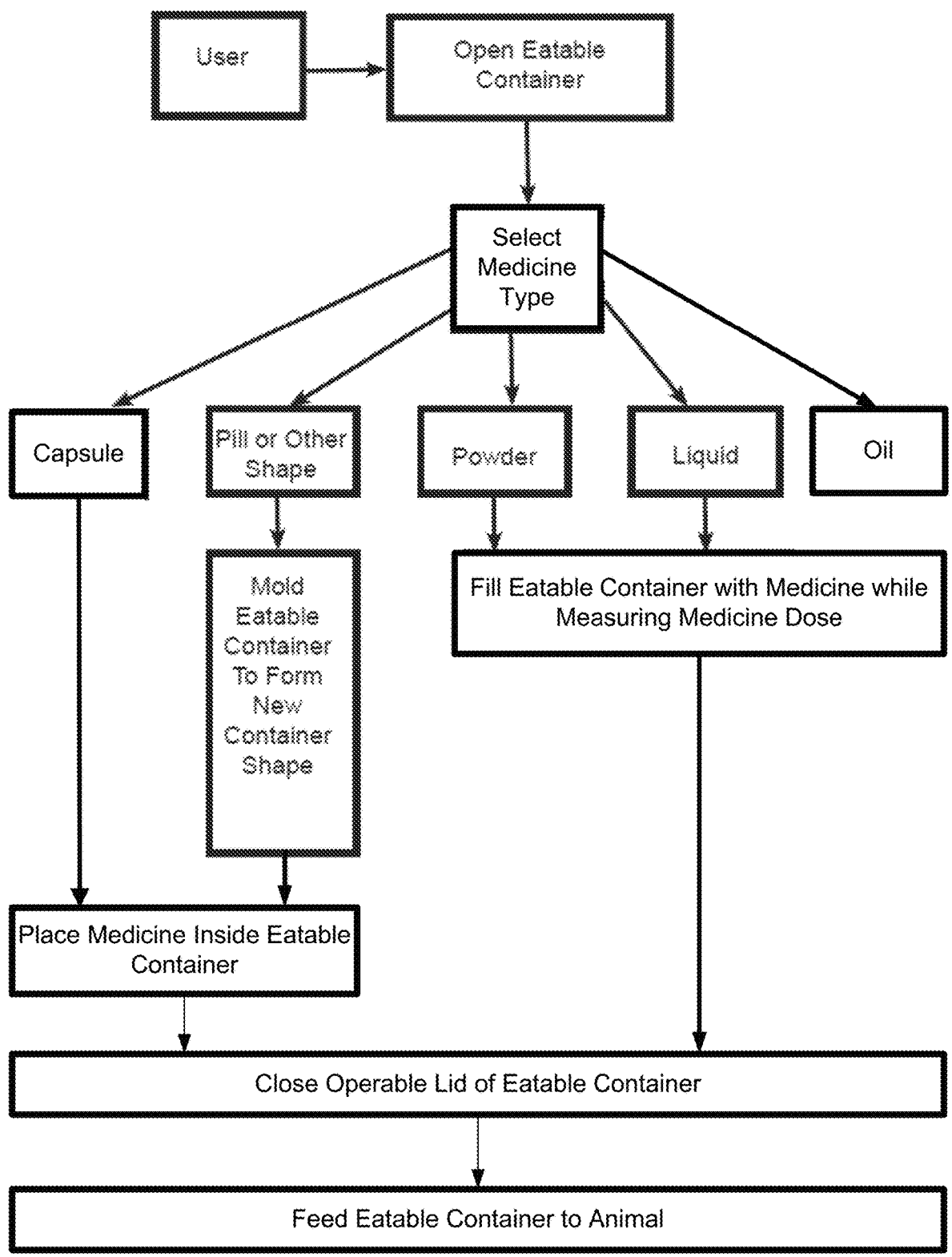
FIG. 51 is a use-flowchart of the flexible multi-function edible animal medicine container, showing the multiple paths of use for the multi-function of the present invention.

FIG. 51 is a flow chart showing the various users paths that a user may use various edible containers of the present invention in a multi-function manner. By selecting a particular medicine to use, the user may follow a different function of the present invention in order for it to function with the particular medicine selection by the user.

Figure 52:
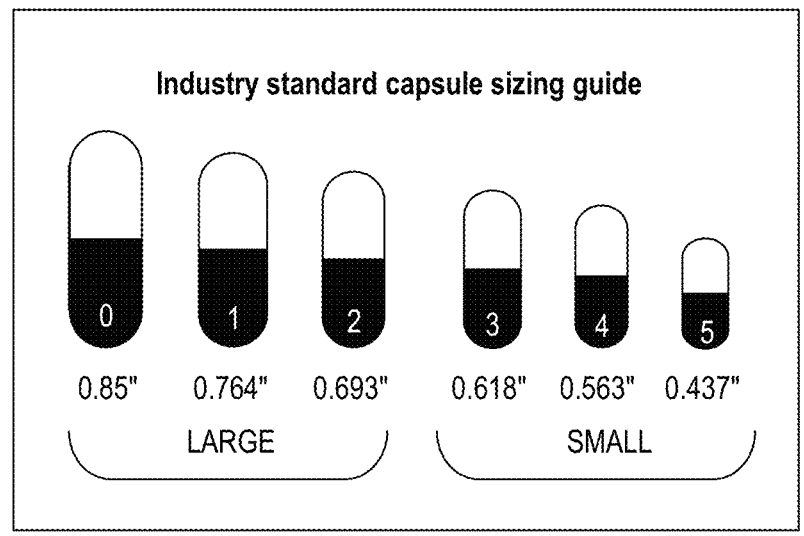
FIG. 52 is a chart showing the industry standard of capsules together with a perspective view of two of the multi-function edible animal medicine container of FIG. 41, in an open state.

In at least some embodiments, edible pet medicine containers are provided in different sizes to accommodate different medicine sizes or dosages. For example, FIG. 52 illustrates the various capsule pill sizes that are typically used in the industry together with a two-size implementation of the edible pet medicine container of FIGS. 41-46.

Figure 53:
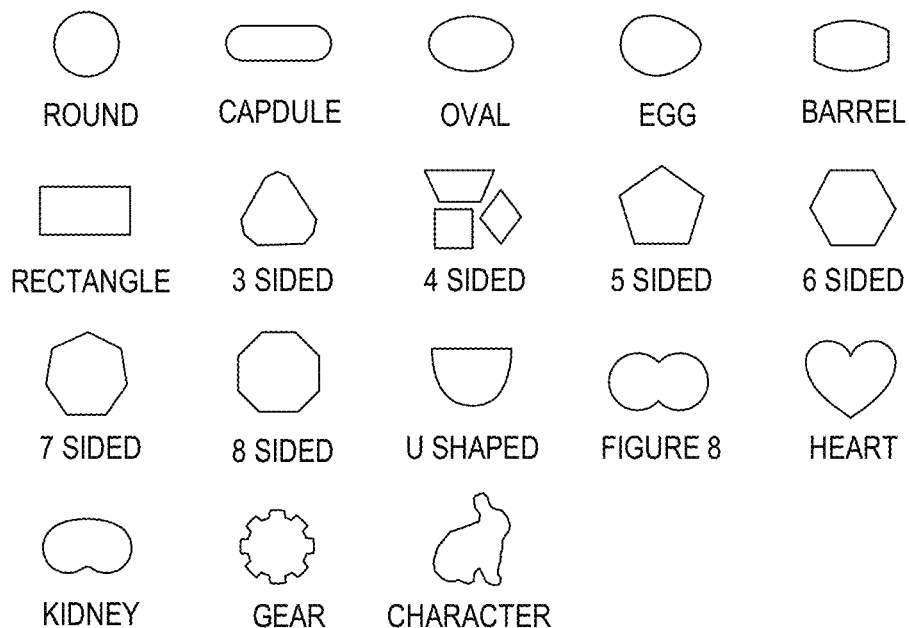
FIG. 53 is a chart showing various industry pill shapes that may be inserted into the multi-function edible animal medicine container.
Figure 54:
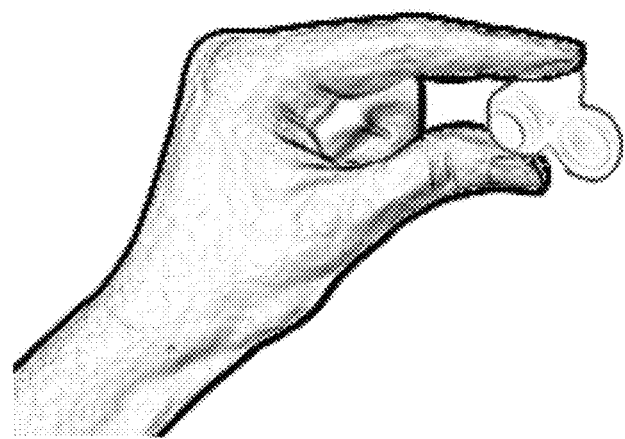
FIG. 54 is a perspective view of the flexible multi-function edible animal medicine container of FIG. 41, with a user pinch molding the present invention for multi-function.
Figure 55:
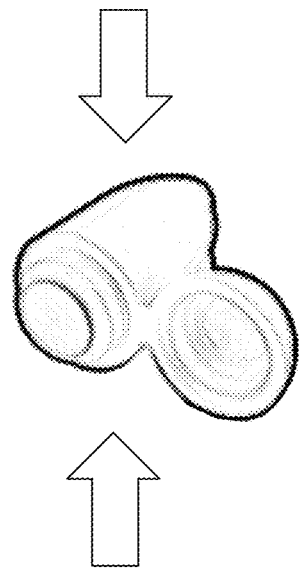
FIG. 55 is a perspective view of the flexible multi-function edible animal medicine container of FIG. 54, showing the pinching forces to molding the present invention for multi-function.

FIG. 53 illustrates various pill shapes that are typically used and found in the industry that can be used with the present invention.

Figure 56:
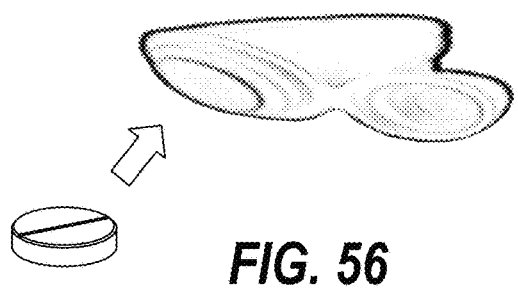
FIG. 56 is a perspective view of the flexible multi-function edible animal medicine container of FIG. 54, in a different molded shape, after being molded per FIG. 55, with a disk pill shape being inserted into the present invention.
Figure 57:
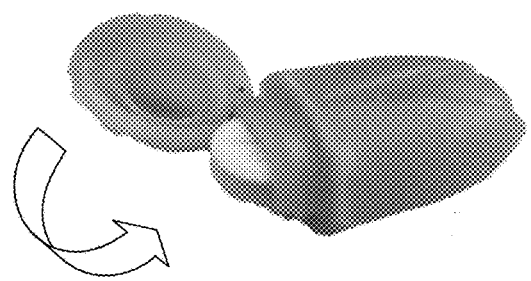
FIG. 57 is a perspective view of the flexible multi-function edible animal medicine container of FIG. 56 with a disk pill shape inserted into the present invention and the lid being moved to a closed position.
Figure 58:
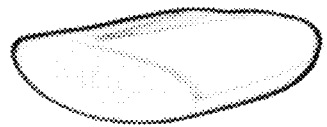
FIG. 58 is a perspective view of the flexible multi-function edible animal medicine container of FIG. 56, in a closed state with a disk pill medicine shape inside.

In at least some of the embodiments described and/or illustrated herein, the edible pet medicine container is sufficiently flexible that it may be manually molded or otherwise re-shaped to accommodate different sized and shaped medicines, such as those show in FIG. 53. For example, as shown in FIGS. 54-58, a user may apply force with whatever means, such as by pinching the container, to form the container into different shapes to function for various medicine shapes. As shown, the shape of the medicine shown in FIG. 56 and FIG. 57 is a disk pill shape. Once the desired shape is formed by the user, the user may the insert the medicine into the edible container and then close the present invention with the cap, as shown in FIG. 57. The edible container and present invention is shown in the closed position in FIG. 58.

Figure 59:
FIG. 59 is a perspective view of the flexible multi-function edible animal medicine container of FIG. 41, in a closed state where a canine is holding the present invention with the teeth grooves.

Notably, various of the edible pet medicine containers described and/or illustrated herein include surface textures, including gripping edges, that make it easier to handle the containers and/or make it easier for a pet to handle it. For example, FIG. 59 is an illustration of a dog holding the edible pet medicine container of FIGS. 41-46 between its teeth using exterior teeth grooves on the surface thereof. The surface texture (here, the grooves) make it more readily possible for the animal to carry the container to consume it in a comfortable location.

Figure 60:
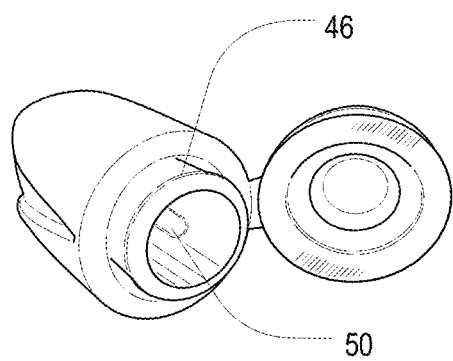
FIGS. 60 and 61 are perspective views of another alternative edible pet medicine container, shown in an open state, in accordance with one or more preferred embodiments of the present invention.
Figure 61:
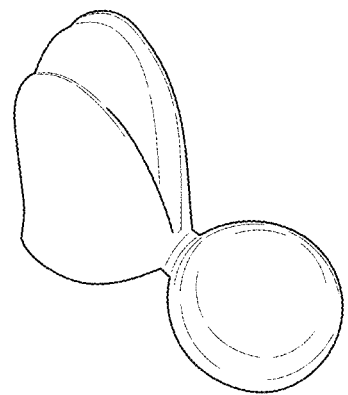
Figure 62:
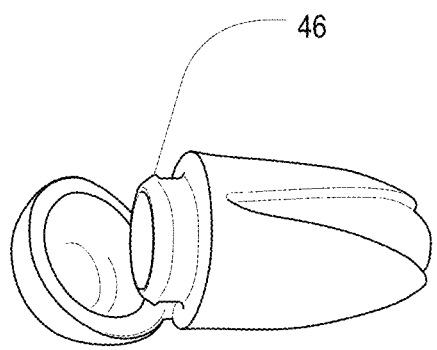
FIG. 62 is a perspective view of the edible pet medicine container of FIG. 60, shown in a partially closed state.
Figure 63:
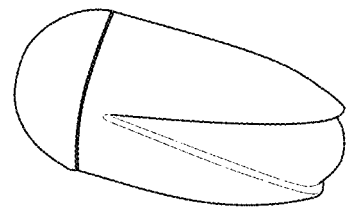
FIG. 63 is a perspective view of the edible pet medicine container of FIG. 60, shown in a fully closed state.

FIGS. 60 and 61 are perspective views of another alternative edible pet medicine container, shown in an open state, in accordance with one or more preferred embodiments of the present invention; FIG. 62 is a perspective view of the edible pet medicine container of FIG. 60, shown in a partially closed state; and FIG. 63 is a perspective view of the edible pet medicine container of FIG. 60, shown in a fully closed state. As shown therein, the container includes a housing, defining an interior, and a hinge or tether. The housing includes an upper shell and a lower shell which are of different sizes. As perhaps best illustrated in FIG. 62, the open face of each shell has a respective peripheral ledge and a central hollow. Surrounding the central hollow of the upper (smaller) shell, but interior from the peripheral ledge, is a recessed ledge, while surrounding the central hollow of the lower (larger) shell, but interior from the peripheral ledge, is a standing wall or higher-level ledge. The various ledges are shaped and sized to fit together as described below.

Figure 64:
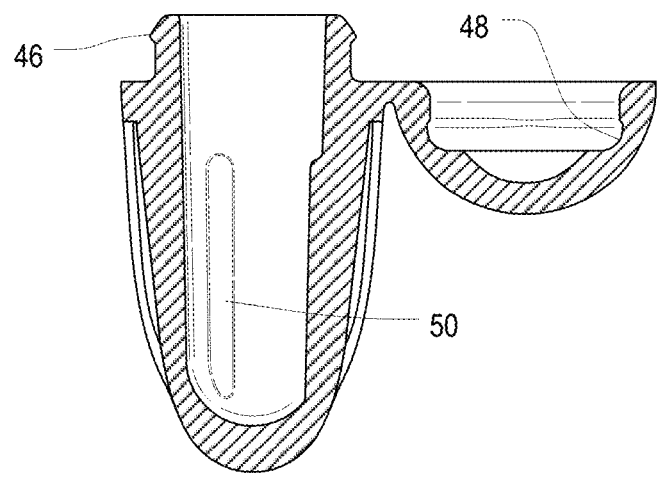
FIG. 64 is a side cross-sectional view of the edible pet medicine container of FIG. 60.
Figure 65:
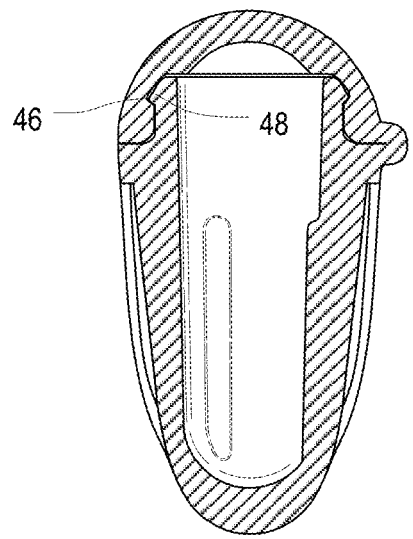
FIG. 65, which is a side cross-sectional view of the edible pet medicine container of FIG. 63.

FIG. 64 is a side cross-sectional view of the edible pet medicine container of FIG. 60. The various ledges may be seen more clearly in FIG. 64. The two shells may be fit together as shown in FIG. 65, which is a side cross-sectional view of the edible pet medicine container of FIG. 63. As shown therein, the standing wall or higher-level ledge of the lower shelf fits neatly into the recessed ledge on the upper shell, with the peripheral ledges meeting one another. In this closed state, the central hollows together form an interior.

Due to the slightly flexible nature of the material from which the two halves are made, the respective ledges are thereby coupled together and retained in place via friction fit, thereby providing a closed and sealed or semi-sealed interior in which medicines, vitamins, or other materials may be filled, loaded or otherwise disposed for ingestion by an animal 14. Such an interlock or coupling advantageously prevents or discourages the container from being opened while it is still in the animal's mouth (i.e., before it has been swallowed). It advantageously also serves to deter the animal 14 from eating only the container and spitting out the pill or medicine contained inside.

As perhaps best shown in FIGS. 64 and 65, this edible pet medicine container includes an improved closure mechanism, wherein a rib, lip, or the like 46 extends around the periphery of the opening into the central opening of the lower (larger) shell, and a corresponding groove 48 extends around the periphery of the recessed ledge within the upper (smaller) shell. As shown in FIG. 65, the lip 46 fits snugly into the groove 48 when the upper shell is installed on the lower shell, thereby providing additional retentive force beyond that provided by the friction fit of the respective ledges and walls. The additional interlocking structures also further insulate the medicine disposed inside the container to prevent objectionable odors from escaping or, in the case of liquid medicines, to prevent leaks. Notably, although the lip 46 may extend completely around the periphery as illustrated, segmented lip or rib sections may instead be utilized in some embodiments, although discontinuities may have an impact on the insulative effect. Furthermore, although retention is improved through the use of the groove corresponding to the lip, some benefit may be achieved without the presence of the groove, at least to the extent that the opening in the upper shell may be molded around the lip 46.

Because the two shells are of different design (e.g., the upper shell has a recessed ledge, while the lower shell has a standing ledge), it is necessary for each container to utilize one upper shell and one lower shell. The hinge helps the user 12 avoid fumbling for a pair of matching shells by clearly linking together one upper shell and one lower shell. The hinge, as well as the two shells, may be made of materials similar to those of other shells and hinges or tethers described herein. Further, because the two shells create a sealed or semi-sealed interior when coupled together, this container may be utilized to hold a liquid, such as a liquid medicine, in a manner similar to that of the container 110 of FIGS. 9 and 10.

In some embodiments, an interior retention system is provided to keep the medication held inside the container, even when the cap of the container has been broken or chew off by the animal. In various example, the interior retention system can be one-way barbs, coupling surface tension, vacuum suction, retention ribs, or any other methods or means known in the industry to retain an object inside a contained area.

Figure 49:
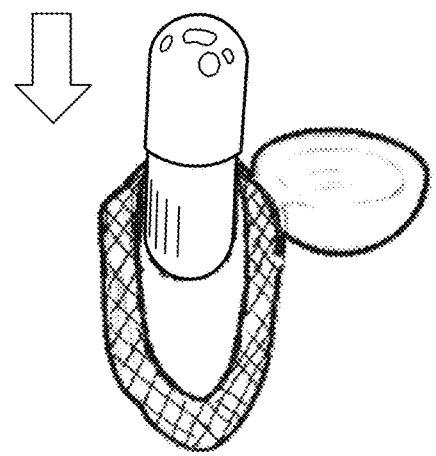
FIG. 49 is a section view of the flexible multi-function edible animal medicine container of FIG. 41 with a medicine capsule being inserted into the present invention forming a vacuum chamber which is formed by the interior of the edible container and the exterior of the medicine capsule.
Figure 48:
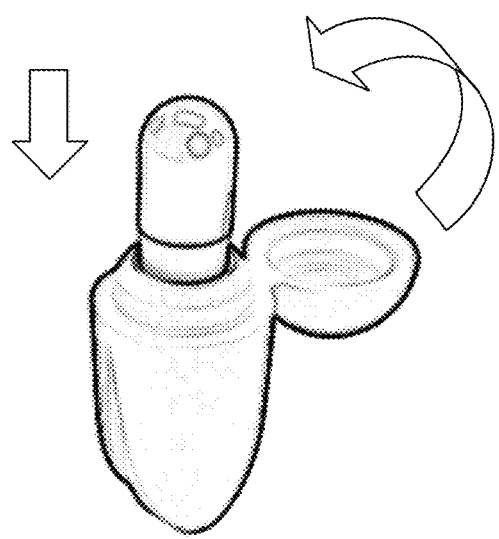
FIG. 48 is a perspective view of the flexible multi-function edible animal medicine container of FIG. 41 with a medicine capsule being inserted into the present invention and the lid being moved to a closed position.
Figure 50:
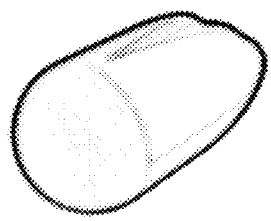
FIG. 50 is a perspective view of the flexible multi-function edible animal medicine container of FIG. 41, in a closed state with a medicine capsule inside.
Figures 66, 67:
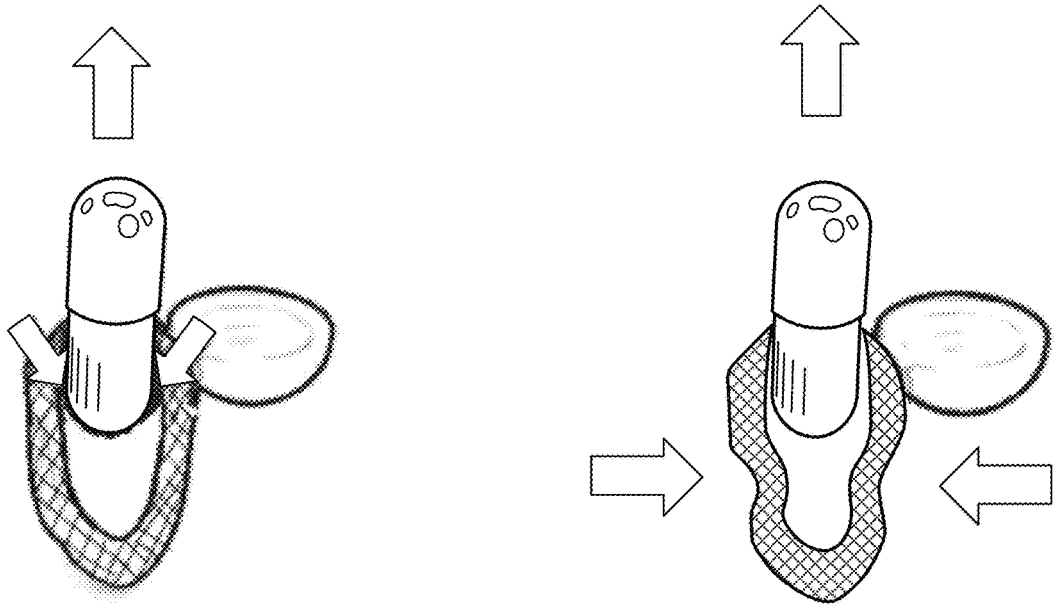
FIG. 66 is a section view of the present invention showing the interior retention system in the form of surface tension.
FIG. 67 is a section view of the present invention showing the interior retention system in the form of interior vacuum chamber with suction.

FIG. 66 is a schematic view of the pill and container of FIG. 49, illustrating use of an interior retention system wherein the outer diameter sides of the medicine capsule frictionally fit into the interior diameter of the eatable container. The friction fit that is produced between the exterior of the medicine capsule and the interior of the eatable container, provides a force that assists in holding a pill or capsule in place in the eatable container. Since the eatable container is flexible, the eatable container can be manually molded, so as to adjust the interior shape and interior diameter of the container to match the shape and area of the intended medicine capsule or pill to be used, thus the eatable container is able to generating frictional forces for various capsule and pill sizes to retain them.

FIG. 67 is a schematic view of the pill and container of FIG. 49, shown after being manually molded to match the shape of the pill. As shown therein, the lower shell can be molded to fit tightly around the pill or capsule such that any attempted removal of the pill effectively creates a vacuum chamber, where the flexible eatable container creates a suction force within the eatable container. The suction force that is produced in the vacuum chamber of the eatable container, is generated when the flexible sides of the eatable container bend, and with such a bending force, creates a suction force when the medicine capsule is being attempted for removal. Thus, via the suction force that is generated within the vacuum chamber of the eatable container, assists in holding a pill or capsule in place.

Figure 70:
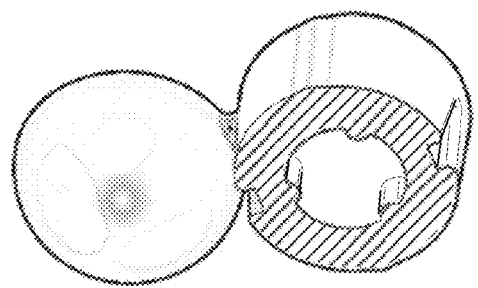
FIG. 70 is an isometric section view of the present invention showing the interior retention system in the form of retention ribs.
Figure 69:
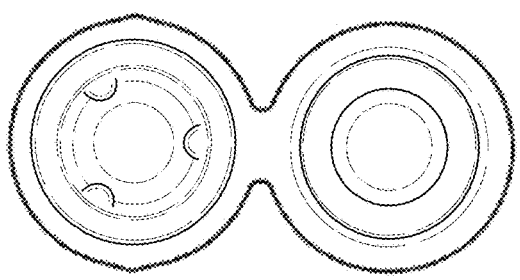
FIG. 69 is a section view of the present invention showing the interior retention system in the form of retention ribs.
Figure 68:
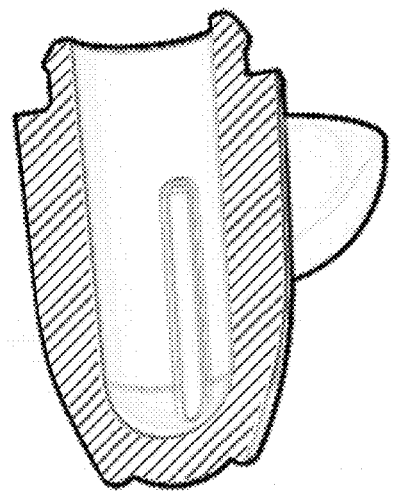
FIG. 68 is an isometric section view of the present invention showing the interior retention system in the form of retention ribs.

In at least some embodiments, an internal retention system includes internal surface features to assist with holding a pill or capsule in place. In this regard, FIGS. 68-70 are a front sectional view, a top view, and a bottom sectional view of the edible pet medicine container of FIG. 61. As shown therein, three ribs 50 run generally longitudinally along the interior surface of the larger (bottom) shell. The ribs allow the container to accommodate of variously-sized and -shaped pills and the like that can be inserted into the container, while retaining said medicine inside the container. Advantageously, larger pills may be forced into the central hollow to take full advantage of the volume thereof, while smaller pills are held more gently between the ribs while making less contact with the walls of the hollow, thereby preventing the pill from rattling around inside the hollow and making the pill-holding container less desirable to a pet. In addition, the ribs help to create an air gap between the pill and the walls of the shell, thereby making it easier to maneuver the pill into the shell. Notably, although ribs are shown, it will be appreciated that internal retention features of other shapes may additionally or alternatively be utilized.

Figure 71:
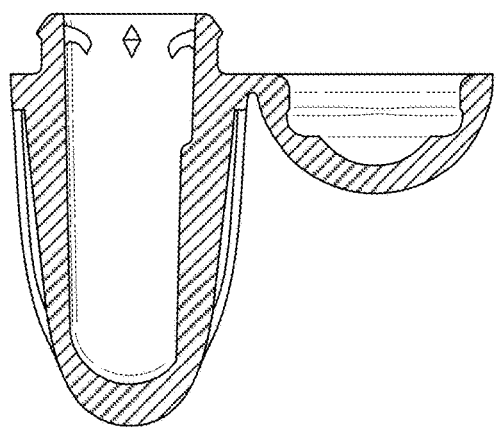
FIG. 71 is a section view of the present invention showing the interior retention system in the form of multiple one-way barbs in a single series.
Figure 72:
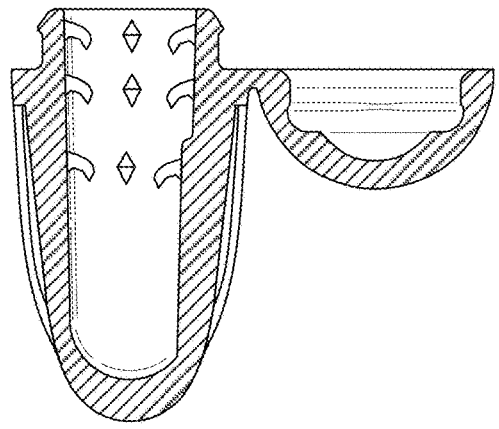
FIG. 72 is a section view of the present invention showing the interior retention system in the form of multiple one-way barbs with multiple series.

In at least some embodiments, an internal retention system includes "one-way" structures to assist with holding a pill or capsule in place. In this regard, FIGS. 71 and 72 are side cross-sectional views of two other alternative edible pet medicine containers, each shown in an open state, in accordance with one or more preferred embodiments of the present invention. The containers in FIGS. 71 and 72 include one or more sets of one-way barbs. FIG. 71 shows a single set of one-way barbs, while FIG. 72 shows multiple sets of one-way barbs. These one-way barbs assist in holding a pill or capsule in place inside the eatable container, and allow for the accommodation of various sized pills that can be inserted into the eatable container. The barbs include tooth-like structures at the ends of flexible arms that are deflected inward as a pill is inserted but which tend to dig into surfaces of the pill to prevent the pill from being withdrawn.

With an interior retention system with various system embodiment described above and herein, even when the cap of a closed eatable container is chewed or broken off by an animal, the interior retention system helps retain the pill or capsule inside the edible container, while the container is being chewed and swallowed by the animal being given the medication. The interior retention system can be one-way barbs, coupling surface tension, vacuum suction, retention ribs, or any other methods or means known in the industry to retain an object inside a contained area.

Figure 73:
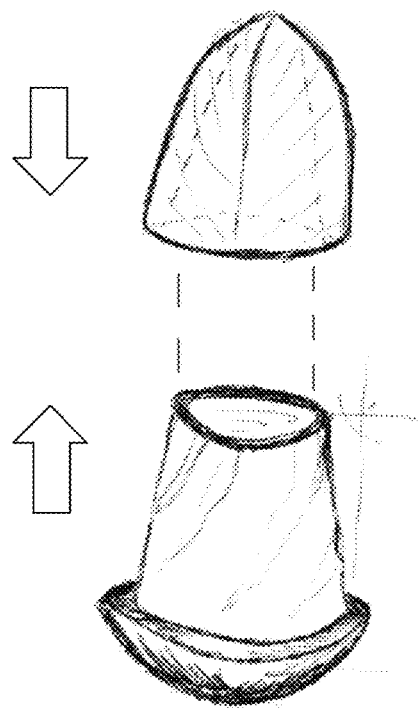
FIG. 73 is a perspective view of another alternative of the flexible multi-function edible animal medicine container with an extended male flange design.
Figure 74:
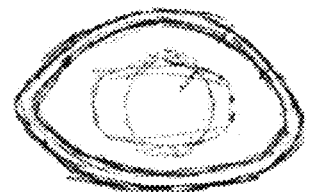
FIG. 74 is a section view of the flexible multi-function edible animal medicine container of FIG. 73, with a capsule and pill shaped medicine inside.
Figure 75:
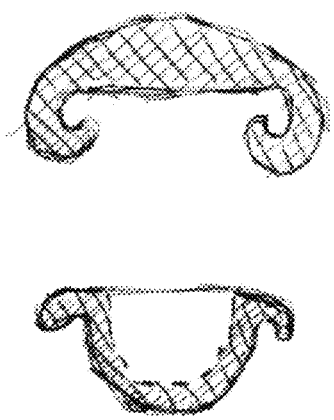
FIG. 75 is a section view of another alternative of the flexible multi-function edible animal medicine container with a horizontal slide closure design.
Figure 76:
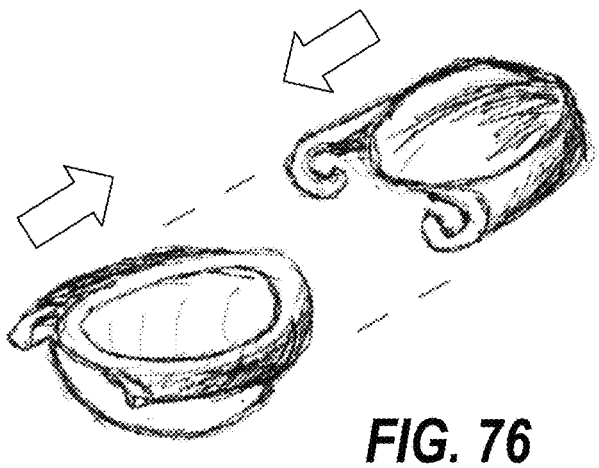
FIG. 76 is a perspective view of the flexible multi-function edible animal medicine container of FIG. 75, being set to a closed position.

In some embodiments, other closure mechanisms may be substituted for those described and/or illustrated thus far. In one example, FIGS. 73 and 74 are conceptual illustrations of a closure mechanism featuring an extended male and female coupling where there is a significant overlap for added security. In another example, FIGS. 75 and 76 are conceptual illustrations of a closure mechanism where the edible container is closed by horizontally siding a lid closure over the containment areas.

Figure 77:
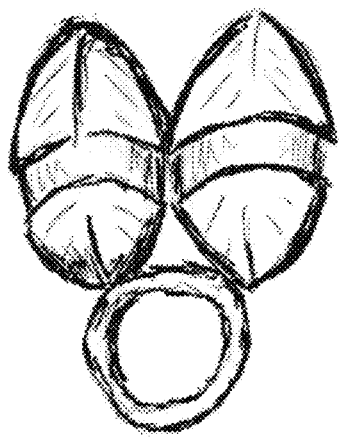
FIG. 77 is a top view of another alternative of the flexible multi-function edible animal medicine container with a slide-ring closure design.
Figure 78:
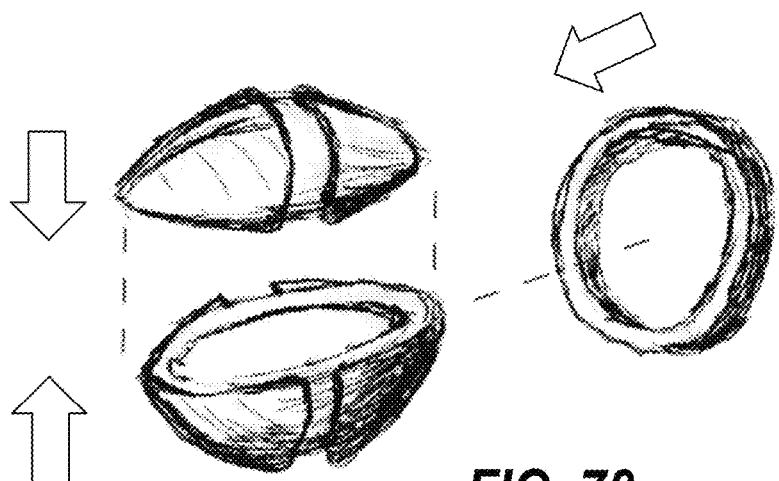
FIG. 78 is a perspective view of the flexible multi-function edible animal medicine container of FIG. 77, being set to a closed position, where the slide-ring locks the two halves together.
Figure 79:
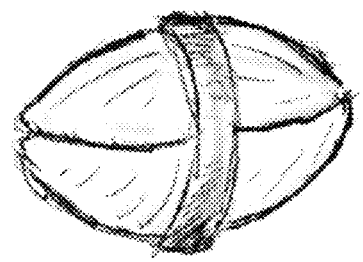
FIG. 79 is a perspective view of the flexible multi-function edible animal medicine container of FIG. 77, in a closed position.
Figure 80:
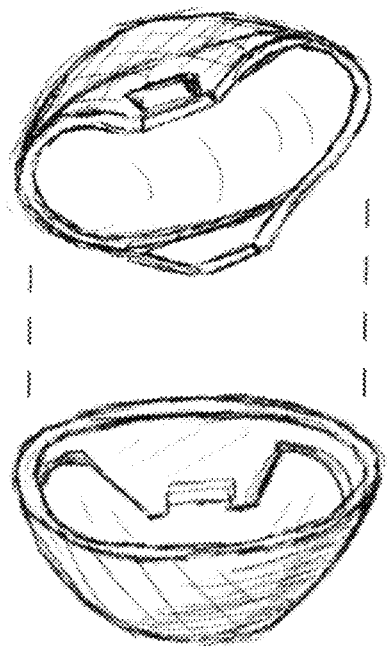
FIG. 80 is a perspective view of another alternative of the flexible multi-function edible animal medicine container with a dual extended flange closure design.
Figure 81:
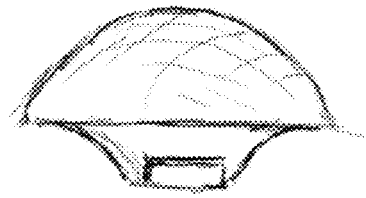
FIG. 81 is a side view of the top portion of the flexible multi-function edible animal medicine container of FIG. 80.

In another example, FIGS. 77-79 are conceptual illustrations of a closure mechanism where a locking ring fits around two shell halves to lock the edible container closed. In at least some embodiments of such a mechanism, the three primary elements are molded together, as shown in FIG. 77, and are then broken apart prior to use. The user then places the medicine inside the edible container and joins the two halves together. Once the two halves are joined, the user slides the locking ring over the two halves to lock the edible container closed, as shown in FIG. 79.

Figure 82:
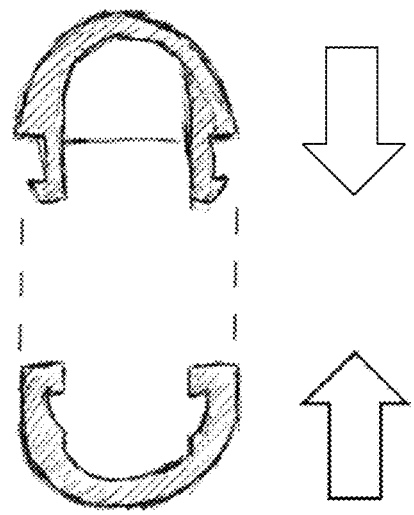
FIG. 82 is a section view of the flexible multi-function edible animal medicine container of FIG. 80, being moved to a closed state.
Figure 83:
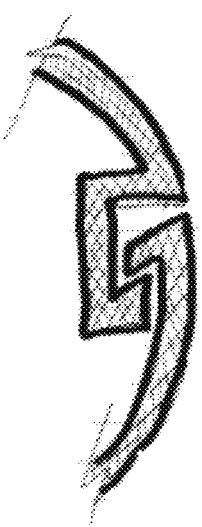
FIG. 83 is a detail section view of the locking design of the flexible multi-function edible animal medicine container of FIG. 80.

In another example, FIGS. 80-83 are conceptual illustrations of a closure mechanism in which there is an extended fastening male structure that is used to extend into the female portion of the edible container for added security when locked closed, as shown in FIG. 82. As shown in FIG. 82, this fastening system is a one-way system, where once the medicine is placed inside the edible container and the container is closed, the closure system locks and may not be re-opened.

Figure 84:
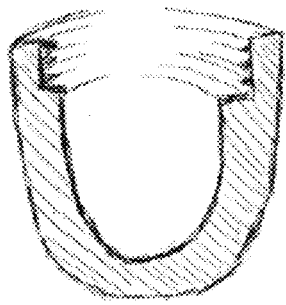
FIG. 84 is a section view of the female portion of another alternative of the flexible multi-function edible animal medicine container with a zip-lock closure design.
Figure 85:
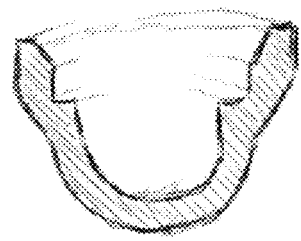
FIG. 85 is a section view of the female portion of another alternative of the flexible multi-function edible animal medicine container with a dual wedge closure design.
Figure 86:
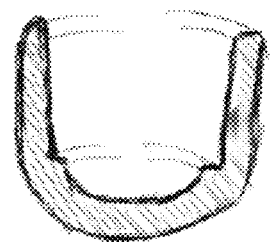
FIG. 86 is a section view of the female portion of another alternative of the flexible multi-function edible animal medicine container with an extended wedge closure design.

In other examples, FIG. 84 is a conceptual illustration of a closure mechanisms wherein the female portion includes a zip-lock fastener; FIG. 85 is a conceptual illustration of a closure mechanisms wherein the female portion includes a dual wedge fastener; and FIG. 86 is a conceptual illustration of a closure mechanisms wherein the female portion includes an extended overlap flange design. Each of these female portions shown would then have the corresponding male portion of the edible container as well, but such male portions are not shown in the drawings.

Figure 87:
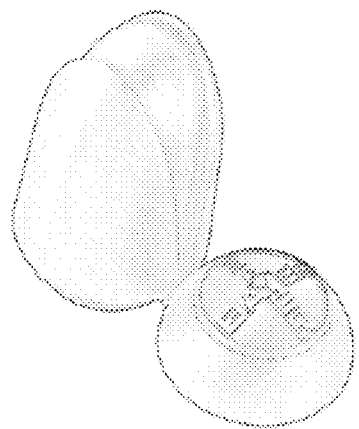
FIG. 87 is a perspective view of another alternative of the flexible multi-function edible animal medicine container with a graphic image embossed on the exterior of the present invention.

In some embodiments, edible pet medicine containers may include a logo, written text, or the like on one or more outside surface thereof. The logo or written text can include, but is not limited to, to sizing information, branding information, instructions, marketing information and the like. For example, FIG. 87 is a bottom perspective view of an edible pet medicine container similar to that of FIG. 61, but shown with a common medicine brand printed on the end of the upper shell.

To use the, the present invention according to another aspect is a method of administering a medicine or other ingestible material to an animal, including: providing an edible animal medicine container having an edible housing, including two shells connected by a hinge or tether, defining an interior; opening the two hinged or tethered shells; loading medicine or other ingestible material into the interior of the housing, where the interior retention system of the housing additionally retains the medicine; closing the two shells together such that the medicine or other ingestible material is retained inside; and delivering the closed container to an animal such that the medicine or other ingestible material remains within the housing as the container enters the digestive tract of the animal.

Figure 88:
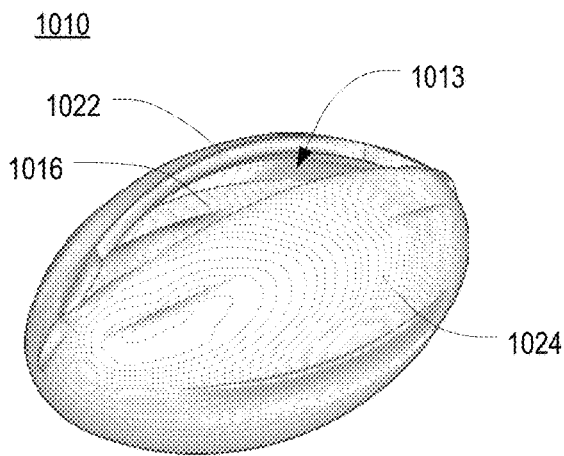
FIG. 88 is a perspective view of another alternative edible pet medicine container, shown in an open state, in accordance with one or more preferred embodiments of the present invention.
Figure 89:
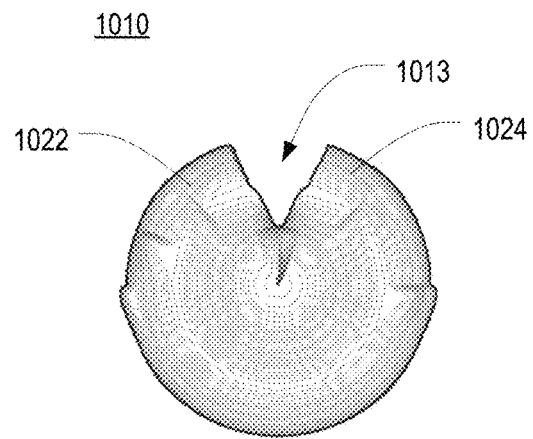
FIG. 89 is an end view of the edible pet medicine container of FIG. 88.
Figure 90:
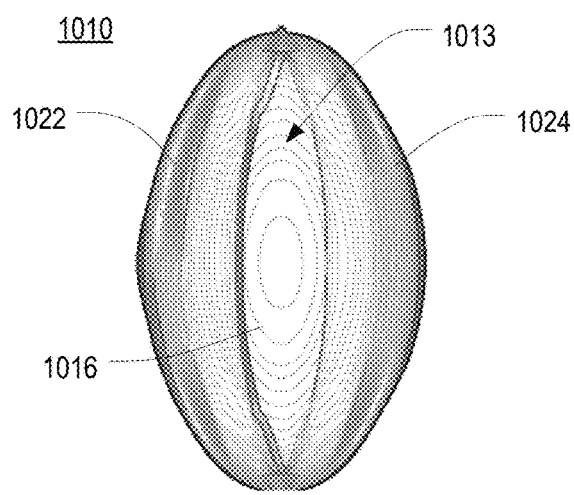
FIG. 90 is a top view of the edible pet medicine container of FIG. 88.
Figure 91:
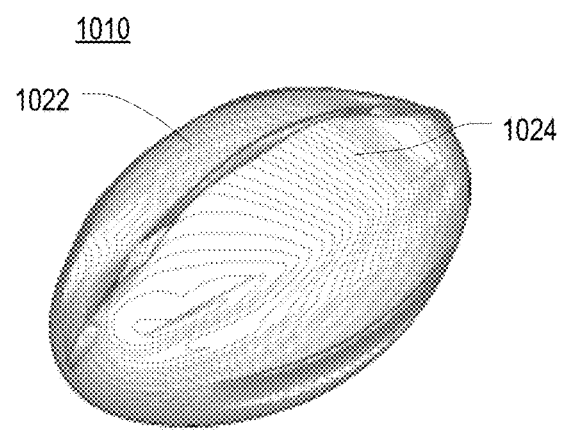
FIG. 91 is a perspective view of the edible pet medicine container of FIG. 88, shown in a closed state.

FIG. 88 is a perspective view of another alternative edible pet medicine container 1010, shown in an open state, in accordance with one or more preferred embodiments of the present invention, while FIGS. 89 and 90 are an end view and a top view, respectively, of the edible pet medicine container 1010 of FIG. 88. As shown therein, the container 1010 includes two shells or halves 1022,1024 that are integrated with one another or connected together to create an interior 1016 that is accessible only via a temporary gap opening 1013. The interior 1016 is large enough to accommodate a pill 18 or other ingestible material therein. The container halves 1022,1024 are produced in such a way as to be softer and more flexible than in some other embodiments such that the halves 1022,1024 may be squeezed, pinched, clamped or otherwise adjusted relative to each other to close the gap opening 1013 and entrap the pill 18 or other ingestible material inside. In this regard, FIG. 91 is a perspective view of the edible pet medicine container 1010 of FIG. 88, shown in a closed state. In at least some of these embodiments, squeezing or otherwise adjusting the halves 1022,1024 further creates at least a temporary water seal to prevent liquid medicine or the like from leaking out.

FIG. 92 is a perspective view of another alternative edible pet medicine container 1110, shown in a closed state, in accordance with one or more preferred embodiments of the present invention, while FIG. 93 is an end view of the edible pet medicine container 1110 of FIG. 92. As shown therein, the container 1110 includes two shells or halves 1122,1124 that are integrated with one another or connected together to create an interior 1116 (shown in FIG. 94) that is accessible only via a temporary gap opening 1113 that is initially provided in a closed state. The interior 1116 is large enough to accommodate a pill 18 or other ingestible material therein. The container halves 1122,1124 are produced in such a way as to be softer and more flexible than in some other embodiments, but more resilient than the container 1010 of FIGS. 88-91, such that ends 1123,1125 of the container 1110 may be squeezed, pinched, clamped or otherwise adjusted relative to each other to force the gap opening 1113 to pop open and remain open for as long as force continues to be applied. In this regard, FIG. 94 is a perspective view of a user 12 squeezing the edible pet medicine container 1110 of FIG. 92 into an open state. As shown therein, a pill 18 has been inserted through the gap opening 1113 so as to be carried in the interior 1116 of the container 1110. Once the ends 1123,1125 are released, the container 1110 is biased to return to its initial state, as shown in FIG. 92, thereby entrapping the pill 18 or other ingestible material inside.

FIG. 95 is a side view of another alternative edible pet medicine container 1210, shown in an initial state, provided in the shape of a whimsical character in accordance with one or more preferred embodiments of the present invention. Functionally, the container 1210 of FIG. 95 is somewhat similar to the container 810 of FIGS. 35-37, wherein two shells 1222,1224 are initially connected along one side but may be broken apart and maneuvered relative to one another to enclose a pill 18 or other ingestible material inside. In this regard, FIG. 96 is a side view of the edible pet medicine container 1210 of FIG. 95, shown in a separated state, while FIG. 97 is a perspective view of the edible pet medicine container 1210 of FIG. 96, shown in a closed state. Notably, however, the container 1210 of FIGS. 95-97 is rendered in a whimsical shape, such as that of the head of a cartoon cat or other figure. Such an arrangement may aid in marketing efforts, consumer adoption, or the like.

In at least some embodiments, such as the embodiment of FIGS. 29-34, the upper and lower halves are of substantially the same size, while in other embodiments, such as the embodiment of FIGS. 11 and 12, the upper and lower shells are of unequal size. In some of these embodiments, the upper and lower shells have different sizes to accommodate different dosage amounts, but different sizes could be used for other purposes as well. In at least some commercial embodiments, edible pet medicine containers may be made commercially available in different sizes for different purposes, such as facilitating the measurement of different dosage amounts, providing different sizes for different size animals 14, or to imitate different types of pet food or edible pet treats. In some of these commercial embodiments, edible pet medicine containers of different sizes are provided in a single package, while in other commercial embodiments, each package contains edible pet medicine containers of only a single size.

In at least one contemplated commercial embodiment, an edible pet medicine container is supplied in the form shown in FIGS. 19-28 and/or the form shown in FIGS. 29-34. Such a container may be approximately 1.3 inches long, 0.75 inches wide, with raised walls or ledges and recessed ledges that are approximately 0.075 inches tall or deep, and each half has a volume of one teaspoon. If the container is supplied in the form shown in FIGS. 19-28, the hinge may be approximately 0.20 inches wide, approximately 0.25 inches long, and approximately 0.04 inches thick.

One material suitable for use as the base material for the construction of the containers described herein is BEP100, available from Biosphere Industries, LLC of Carpinteria, Calif. BEP100 is a high performance, starch-based molding material that can be baked into rigid shapes similar to the process of making waffles or ice cream cones and is well-suited for molded shape pet treats. Various flavorings, colors, and the like may be added as desired, and products of different flavors, colors, and the like may be included in a commercial product line. Other edible starch-based molding materials can be used, such as potato starch or other edible starches, which then can be formed into molded shapes for pet treats via injection molding. Other materials or ingredients for making and shaping the containers may be used, for flexible or ridged construction such as gelatins, fats, animal fats, proteins, vegetable based materials, meat based materials, gummy, corn based, grain, sugar based, candy, flower based, chia seed based, dough based, and the like and as known in the industry. Other manufacturing methods and materials for molding and shaping the containers may be used, such as pour molding, dye cut, press molding, 3D printing, additive manufacturing, and the like and as known in the industry.

In at least some embodiments, interlocking features (such as the various recesses, ledges, pegs, slots, and the like described herein) are provided so as to create sufficient coupling force to ensure that the various containers using such features are sealed against water leakage, at least to some degree, at least temporarily. More particularly, although various containers may, in at least some cases, be separated by hand by applying sufficient force to overcome the frictional forces holding them together (in the form of the various interlocking features being coupled together), such containers may be designed to withstand leakage of a liquid medicine or other ingestible material when placed inside, at least for a period of time from the moment the two halves are fully coupled together until the closed container is ingested by a pet 14. Preferably, the coupling is strong enough to withstand internal hydrostatic pressure up to 1 PSI. More preferably, the coupling is strong enough to withstand internal hydrostatic pressure up to 5 PSI.

In various embodiments, containers of the present invention may be utilized with dogs and other canines, housecats and other felines, pigs, horses, and a wide variety of other animals, including at least some non-mammals.

Based on the foregoing information, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof.

What is claimed is:

1. An edible animal medicine container for delivering medicine or other ingestible material, contained therein, to an animal, comprising:
    a first edible housing shell that includes a first opening defined by a first peripheral ledge wherein the first peripheral ledge has a periphery, wherein the periphery of the first peripheral ledge is surrounded by a second peripheral ledge that is stepped down from the first peripheral ledge, wherein the periphery of the first peripheral ledge is connected to the second peripheral ledge via a first wall, and wherein a peripheral lip is disposed around the first wall and extends outward therefrom;
    a second edible housing shell that includes a second opening defined by a third peripheral ledge, wherein the third peripheral ledge surrounds a fourth peripheral ledge that is recessed into the second opening, and wherein the periphery of the fourth peripheral ledge is connected to the third peripheral ledge by a second wall;
    wherein the second edible housing shell is positionable relative to the first edible housing shell in a closed state to define an interior in which medicine or other ingestible material may be disposed by a user;
    wherein in such closed state the first peripheral ledge, the first wall, and the peripheral lip are inserted into the second opening such that:
        the first peripheral ledge is placed within close proximity of the fourth peripheral ledge inside the second opening,
        the third peripheral ledge is placed within close proximity of the second peripheral ledge, and
        the second wall is placed in contact with the first wall, including the peripheral lip; and
    wherein in such closed state the second edible housing shell is seated and held on the first edible housing shell so as to retain the first and second edible housing shells together and thereby retain the medicine or other ingestible material within the interior until ingested by an animal.

2. The edible animal medicine container of claim 1, wherein a peripheral groove extends into the second wall such that the closed state peripheral lip around the first wall fits into, and is retained in, the peripheral groove of the second wall so as to retain the first and second edible housing shells together.

3. The edible animal medicine container of claim 2, wherein in the closed state, the first peripheral ledge is in direct contact with the fourth peripheral ledge, thereby closing a gap between the first and second edible housing shells.

4. The edible animal medicine container of claim 2, wherein, in at least an initial open state, the two shells are integrally connected together.

5. The edible animal medicine container of claim 4, wherein an edge of the first edible housing shell is initially connected directly to an edge of the second edible housing shell.

6. The edible animal medicine container of claim 5, wherein the edible hinge or tether is adapted to hold the two shells together until the edible hinge or tether is snapped by a user so as to close the two shells.

7. The edible animal medicine container of claim 4, wherein the first and second edible housing shells are connected together at least initially via an edible hinge or tether.

8. The edible animal medicine container of claim 2, wherein the first edible housing shell defines a central hollow, wherein the first opening is in fluid communication with, and provides access to, the central hollow, and wherein the central hollow forms the predominant portion of the interior of the container in the closed state.

9. The edible animal medicine container of claim 8, wherein the second edible housing shell serves as a cap to cover the first opening and the central hollow of the first edible housing shell.

10. The edible animal medicine container of claim 8, wherein the central hollow is defined by interior surfaces of first edible housing shell, and wherein the interior surfaces include a plurality of surface features, extending or rising from surrounding portions of the interior surfaces to receive and retain pill or capsule-form medicine in the central hollow.

11. The edible animal medicine container of claim 10, wherein the surface features are ribs extending longitudinally along the central hollow interior surfaces.

12. An edible animal medicine container for delivering medicine or other ingestible material, contained therein, to an animal, comprising:
  a first edible housing shell that includes a first opening defined by a first peripheral ledge wherein the first peripheral ledge has a periphery, wherein the periphery of the first peripheral ledge is surrounded by a second peripheral ledge that is stepped down from the first peripheral ledge, and wherein the periphery of the first peripheral ledge is connected to the second peripheral ledge via a first wall;
  a second edible housing shell that includes a second opening defined by a third peripheral ledge, wherein the third peripheral ledge surrounds a fourth peripheral ledge that is recessed into the second opening, and wherein the periphery of the fourth peripheral ledge is connected to the third peripheral ledge by a second wall;
  wherein at least one of the first and second edible housing shells defines a central hollow, wherein the first or second opening, respectively, is in fluid communication with, and provides access to, the central hollow, wherein the central hollow is defined by interior surfaces of first or second edible housing shell, respectively, and wherein the interior surfaces include a plurality of surface features, extending or rising from surrounding portions of the interior surfaces to receive and retain pill or capsule-form medicine in the central hollow;
  wherein the second edible housing shell is positionable relative to the first edible housing shell in a closed state to define an interior, including the central hollow, in which medicine or other ingestible material may be disposed by a user;
  wherein in such closed state the first peripheral ledge and the first wall are inserted into the second opening such that:
    the first peripheral ledge is placed within close proximity of the fourth peripheral ledge inside the second opening,
    the third peripheral ledge is placed within close proximity of the second peripheral ledge, and
    the second wall is placed in contact with the first wall; and
  wherein in such closed state the second edible housing shell is seated and held on the first edible housing shell so as to retain the first and second edible housing shells together and thereby retain the medicine or other ingestible material within the interior, including the central hollow, until ingested by an animal.

13. The edible animal medicine container of claim 12, wherein the surface features are ribs extending longitudinally along the central hollow interior surfaces.

14. The edible animal medicine container of claim 13, wherein the ribs receive and retain pill or capsule-form medicine in the central hollow such that an air gap exists between surfaces of the medicine and the surrounding portions of the central hollow interior surfaces.

15. The edible animal medicine container of claim 12, wherein in the closed state, the first peripheral ledge is in direct contact with the fourth peripheral ledge, thereby closing a gap between the first and second edible housing shells and preventing liquids placed in the container from flowing and leaking out of the container.

16. The edible animal medicine container of claim 12, wherein, in at least an initial open state, the two shells are integrally connected together.

17. The edible animal medicine container of claim 12, wherein a peripheral lip is disposed around the first wall and extends outward therefrom, wherein a peripheral groove extends into the second wall such that the closed state peripheral lip around the first wall fits into, and is retained in, the peripheral groove of the second wall so as to retain the first and second edible housing shells together.

* * * * *